(12) United States Patent
Schoenafinger et al.

(10) Patent No.: US 8,871,798 B2
(45) Date of Patent: Oct. 28, 2014

(54) TRICYCLIC PYRIDYL-VINYL PYRROLES AS PAR1 INHIBITORS

(71) Applicant: Sanofi, Paris (FR)

(72) Inventors: Karl Schoenafinger, Alzenau (DE); Henning Steinhagen, Schwalbach am Taunus (DE); Bodo Scheiper, Munich (DE); Uwe Heinelt, Wiesbaden (DE); Volkmar Herrmann, Sandberg (DE); Matthias Herrmann, Hofheim (DE)

(73) Assignee: Sanofi, Paris (FR)

( * ) Notice: Subject to any disclaimer, the term of this patent is extended or adjusted under 35 U.S.C. 154(b) by 0 days.

(21) Appl. No.: 13/652,898

(22) Filed: Oct. 16, 2012

(65) Prior Publication Data

US 2013/0040943 A1 Feb. 14, 2013

Related U.S. Application Data

(63) Continuation of application No. PCT/EP2011/055965, filed on Apr. 14, 2011.

(30) Foreign Application Priority Data

Apr. 16, 2010 (EP) .................................... 10305396

(51) Int. Cl.
| | | |
|---|---|---|
| *C07D 471/14* | (2006.01) | |
| *C07D 487/14* | (2006.01) | |
| *C07D 498/14* | (2006.01) | |
| *A61K 31/407* | (2006.01) | |
| *A61K 31/437* | (2006.01) | |
| *A61K 31/4985* | (2006.01) | |
| *A61K 31/5383* | (2006.01) | |
| *A61P 7/02* | (2006.01) | |

(52) U.S. Cl.
CPC ............ *C07D 471/14* (2013.01); *C07D 487/14* (2013.01); *C07D 498/14* (2013.01)
USPC ........... 514/411; 514/422; 514/423; 548/427; 548/428; 548/429; 548/430; 546/81; 546/84; 546/85; 546/86

(58) Field of Classification Search
CPC .. C07D 471/14; C07D 487/14; C07D 498/14; A61K 31/407; A61K 31/437; A61K 31/4985; A61K 31/5383
USPC .......... 514/411, 422, 423; 548/427, 428, 429, 548/430; 546/81, 84, 85, 86
See application file for complete search history.

(56) References Cited

U.S. PATENT DOCUMENTS

| | | | |
|---|---|---|---|
| 6,063,847 A | 5/2000 | Chackalamannil et al. | |
| 6,326,380 B1 | 12/2001 | Chackalamannil et al. | |
| 2004/0152736 A1 | 8/2004 | Chackalamannil et al. | |
| 2004/0176418 A1 | 9/2004 | Thiruvengadam et al. | |
| 2004/0192753 A1 | 9/2004 | Chackalamannil et al. | |
| 2005/0267155 A1 | 12/2005 | Chelliah et al. | |
| 2006/0063847 A1 | 3/2006 | Matsumura et al. | |
| 2006/0079684 A1 | 4/2006 | Chackalamannil et al. | |
| 2007/0149518 A1 | 6/2007 | Chackalamannil et al. | |
| 2007/0232635 A1 | 10/2007 | Chelliah et al. | |

FOREIGN PATENT DOCUMENTS

| | | |
|---|---|---|
| EP | 1391451 | 2/2004 |
| EP | 1391452 | 2/2004 |
| WO | WO 99/26943 | 6/1999 |
| WO | WO 01/96330 | 12/2001 |
| WO | WO 03/089428 | 10/2003 |
| WO | WO 2006/076564 | 7/2006 |
| WO | WO 2006/105217 | 10/2006 |
| WO | WO 2008/042422 | 4/2008 |
| WO | WO 2009/124103 | 10/2009 |

OTHER PUBLICATIONS

U.S. Appl. No. 13/652,893, filed Oct. 16, 2012, Schoenafinger, et al.
Chackalamannil, et al., Thrombin Receptor (PAR-1) Antagonists as Novel Antithrombotic Agents, Expert Opinion on Therapeutic Patents, vol. 16, No. 4, pp. 493-505, (2006).
Chebanov, et al., Tuning of Chemo- and Regioselectivities in Multicomponent Condensations of 5-Aminopyrazoles, Dimedone, and Aldehydes, Journal of Organic Chemistry, vol. 73, No. 13, (2008), pp. 5110-5118.
Quiroga, et al., Synthesis of 4-Aryl-4,7,8,9-Tetrahydro-6H-Pyrazolo[3,4-b]Quinolin-5-Ones, Journal of Heterocyclic Chemistry, vol. 35, No. 3, pp. 575-578, (1998).
Hollenberg, et al., International Union of Pharmacology,. XXVIII. Proteinase-Activated Receptors, Pharmacological Reviews, vol. 54, No. 2, pp. 203-217, (2002).
Brass, Platelets and Proteases, Nature, vol. 413, pp. 26-27, (2001).
Chintala, et al., Efficacy of SCH 602539, A Selective Thrombin Receptor Antagonist, Alone and in Combination With Cangrelor in a Folts Model of Thrombosis in Anesthetized Monkeys, Eur. Heart J., vol. 28, (Suppl. 1), (2007), pp. 188, Abstract.
International Search Report for WO2011/128421 dated Oct. 20, 2011.

*Primary Examiner* — Sreeni Padmanabhan
*Assistant Examiner* — Irina Neagu

(57) ABSTRACT

This disclosure relates to compounds of formula I:

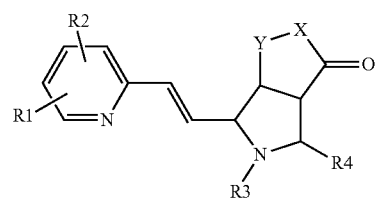

wherein R1, R2, R3, R4, X and Y have the meanings denoted in the disclosure. The compounds of formula I have antithrombotic activity and in particular inhibit the protease-activated receptor 1 (PAR1). The disclosure further relates to a method for producing the compound of formula I and to the use thereof as a pharmaceutical product.

9 Claims, No Drawings

TRICYCLIC PYRIDYL-VINYL PYRROLES AS PAR1 INHIBITORS

This application is a continuation of International Application No. PCT/EP2011/055965, filed Apr. 14, 2011, which is incorporated herein by reference in its entirety; which claims the benefit of priority of European Patent Application No. 10305396.3, filed Apr. 16, 2010.

The invention relates to novel compounds of the formula I

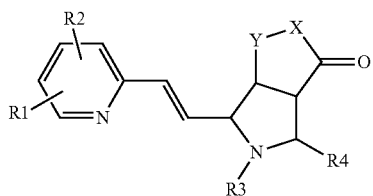

where R1, R2, R3, R4, X and Y have the meaning defined below. The compounds of the formula I have antithrombotic activity and inhibit in particular the protease-activated receptor 1 (PAR1). The invention further relates to a process for preparing the compound of the formula I and the use thereof as medicament.

The protease-activated receptor 1 (PAR1) is a thrombin receptor which belongs to the class of G protein-coupled receptors (GPCR). The gene for PAR1 is located on chromosome 5q13, consists of two exons and covers a region of about 27 kb. PAR1 is expressed inter alia in endothelial cells, smooth muscle cells, fibroblasts, neurons and human blood platelets. On blood platelets, PAR1 is an important receptor of signal transmission and is involved in initiating the aggregation of blood platelets. Activation of the PARs takes place by proteolytic elimination of part of the N terminus of the PARs, thus exposing a new N-terminal sequence which then activates the receptor (M. D. Hollenberg et al., Pharmacol. Rev. 54:203-217, 2002).

The coagulation of blood is a process for controlling blood flow which is essential for the survival of mammals. The process of coagulation and the subsequent breakup of the clot after wound healing has taken place starts after damage to a vessel and can be divided into four phases:

1. The phase of vascular constriction: the blood loss into damaged areas is reduced thereby.

2. The next phase is that of platelet adhesion to the exposed collagen in the subendothelium. This primary adhesion to the matrix activates the platelets, which then secrete various activators which lead to enhancement of the activation. These activators additionally stimulate further recruitment of new platelets to the site of vessel damage and promote platelet aggregation. The platelets aggregate at the site of vessel wall damage and form a still loose platelet plug. Activation of platelets further leads to presentation of phosphatidylserine and phosphatidylinositol along the cell membrane surfaces. Exposure of these phospholipids is essential for binding and activating multienzyme complexes of the blood coagulation cascade.

3. The initially still loose platelet aggregate is crosslinked by fibrin. If the thrombus comprises only platelets and fibrin, it is a white thrombus. If red blood corpuscles are additionally present, it is a red thrombus.

4. After wound healing, the thrombus is broken up by the action of the protein plasmin.

Two alternative pathways lead to the formation of a fibrin clot, the intrinsic and the extrinsic pathway. These pathways are initiated by different mechanisms, but in a later phase they converge to a common pathway of the coagulation cascade. Formation of a red thrombus or a clot on the basis of a vessel wall abnormality without wound is the result of the intrinsic pathway. Fibrin clot formation as response to tissue damage or injury is the result of the extrinsic pathway. Both pathways include a relatively large number of proteins which are known as coagulation factors.

The intrinsic pathway requires coagulation factors VIII, IX, X, XI and XII and also prekallikrein, high molecular weight kininogen, calcium ions and phospholipids from platelets. Each of these proteins activates factor X. The intrinsic pathway is initiated when prekallikrein, high molecular weight kininogen, factor XI and XII bind to a negatively charged surface. This moment is referred to as the contact phase. Exposure to a vessel wall collagen is the primary stimulus of the contact phase. The result of the contact phase processes is conversion of prekallikrein into kallikrein, which in turn activates factor XII. Factor XIIa hydrolyzes further prekallikrein to kallikrein, so that the result is activation. As the activation of factor XII increases there is activation of factor XI which leads to release of bradykinin, a vasodilator. The initial phase of vasoconstriction is terminated thereby. Bradykinin is produced from the high molecular weight kininogen. In the presence of $Ca^{2+}$ ions, factor XIa activates factor IX. Factor IX is a proenzyme which contains vitamin K-dependent, C-carboxyglutamate (GLA) residues. The serine protease activity becomes evident after $Ca^{2+}$ ions have bound to these GLA residues. Several of the serine proteases in the blood coagulation cascade (factors II, VII, IX and X) contain such vitamin K-dependent GLA residues. Factor IXa cleaves factor X and leads to activation to factor Xa. The precondition for the formation of factor IXa is the formation of a protease complex of $Ca^{2+}$ ions and factors VIIIa, IXa and X on the surface of activated platelets. One of the reactions of activated platelets is the presentation of phosphatidylserine and phosphatidylinositol along the surfaces. Exposure of these phospholipids is a precondition for the formation of the protease complex. In this process, factor VIII acts as a receptor for factors IXa and X. Factor VIII therefore represents a cofactor in the coagulation cascade. Activation of factor VIII with formation of factor VIIIa, the actual receptor, requires only a minimal amount of thrombin. As the concentration of thrombin increases, factor VIIIa is finally cleaved further, and inactivated, by thrombin. This dual activity of thrombin in relation to factor VIII leads to the protease complex formation being self-limiting and thus the blood coagulation being localized.

PAR1 and PAR4 play a central role in the activation of human blood platelets by thrombin; activation of these receptors leads to morphological changes in blood platelets, release of ADP and aggregation of the blood platelets (S. Brass, Nature 413:26-27, 2001).

PAR1 inhibitors are described for example in EP 1391451, EP 1391452, U.S. Pat. No. 6,063,847, US 2004/152736, US 2004/176418, US 2004/192753, US 2005/267155, US 2006/063847, US 2006/079684, US 2007/149518, US 2007/232635, U.S. Pat. No. 6,326,380, WO 99/26943, WO 01/96330, WO 03/089428, WO 2006/076564, WO 2006/105217 and WO 2008/042422.

It has been found that the compounds of the formula I show a high specific inhibition of the protease-activated receptor 1. Compounds of the formula I are therefore suitable for prophylactic and therapeutic use in humans suffering from disorders associated with thromboses, embolisms, hypercoagulability or fibrotic alterations. Examples of such disorders are thrombosis, deep vein thrombosis, pulmonary embolisms, cerebral infarction, myocardial infarction, high blood pressure, inflammatory disorders, rheumatism, asthma, glomerulonephritis or osteoporosis. The compounds of the formula I can be employed for secondary prevention and are suitable both for acute and for long-term therapy. The compounds of the formula I can also be employed in combination with active compounds which act by antithrombotic principles different from PAR1.

Accordingly, the invention relates to a compound of the formula I

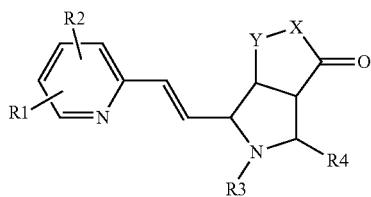

and/or all stereoisomeric or tautomeric forms of the compound of the formula I and/or mixtures of these forms in any ratio, and/or a physiologically acceptable salt of the compound of the formula I, where R1 and R2 are identical or different and are independently of one another hydrogen, —($C_1$-$C_6$)-alkyl, —O—($C_1$-$C_6$)-alkyl, aryl, halogen or hetaryl, where alkyl, aryl and hetaryl are in each case unsubstituted or mono-, di- or trisubstituted independently of one another by F, Cl, Br, CN, —($C_1$-$C_4$)-alkyl, —O—($C_1$-$C_4$)-alkyl, —NH—($C_1$-$C_4$)-alkyl, —N(($C_1$-$C_4$)-alkyl)$_2$, —NH$_2$, —OH, —O—CF$_3$, —S—CF$_3$ or —CF$_3$, or R1 and R2 together with the ring atoms to which they are respectively attached form a 5-membered to 6-membered ring, where the ring consists only of carbon atoms, or 1, 2 or 3 of these atoms are replaced by nitrogen, oxygen or sulfur atoms, where the ring is unsubstituted or mono-, di- or trisubstituted independently of one another by F, Cl, Br, CN, —($C_1$-$C_4$)-alkyl, —O—($C_1$-$C_4$)-alkyl, —NH—($C_1$-$C_4$)-alkyl, —N(($C_1$-$C_4$)-alkyl)$_2$, —NH$_2$, —OH, —O—CF$_3$, —S—CF$_3$ or —CF$_3$;

R3 and R4 together with the ring atoms to which they are respectively attached form a saturated or unsaturated 5-membered to 7-membered ring, where the ring consists only of carbon atoms, or 1 or 2 of these atoms are replaced by O, S, SO, SO$_2$ or N—R5, where the ring is unsubstituted or mono-, di- or trisubstituted independently of one another by F, Cl, —OH, —NH—R7, —($C_1$-$C_4$)-alkyl, —O—($C_1$-$C_4$)-alkyl, —C(O)—O—($C_1$-$C_4$)-alkyl, aryl or hetaryl;

X is N—R6 or O;
Y is C(O), CH$_2$, CH—CH$_3$ or C(CH$_3$)$_2$;
R5 is hydrogen, —C(O)—($C_1$-$C_4$)-alkyl, —C(O)—O—($C_1$-$C_4$)-alkyl, —($C_1$-$C_6$)-alkyl, —($C_2$-$C_4$)-alkyl-O—($C_1$-$C_4$)-alkyl, —($C_2$-$C_4$)-alkyl-OH, aryl or hetaryl,
R7 is hydrogen, —C(O)—($C_1$-$C_4$)-alkyl, —C(O)—O—($C_1$-$C_4$)-alkyl, —($C_1$-$C_6$)-alkyl, —($C_2$-$C_4$)-alkyl-O—($C_1$-$C_4$)-alkyl, —($C_2$-$C_4$)-alkyl-OH, aryl or hetaryl;
R6 is hydrogen, —($C_1$-$C_6$)-alkyl, —($C_3$-$C_7$)-cycloalkyl, —($C_1$-$C_4$)-alkylene-aryl or C(O)—O—($C_1$-$C_4$)-alkyl;

where the term "hetaryl" means ring systems having 4 to 15 carbon atoms which are present in one, two or three ring systems connected together, and which comprise, depending on the ring size, one, two, three or four identical or different heteroatoms from the group consisting of oxygen, nitrogen and sulfur.

The invention furthermore relates to a compound of the formula I, and/or all stereoisomeric or tautomeric forms of the compound of the formula I and/or mixtures of these forms in any ratio, and/or a physiologically acceptable salt of the compound of the formula I, where R1 and R2 are identical or different and are independently of one another hydrogen, —($C_1$-$C_6$)-alkyl, —O—($C_1$-$C_6$)-alkyl, aryl, halogen or hetaryl, where alkyl, aryl and hetaryl are in each case unsubstituted or mono-, di- or trisubstituted independently of one another by F, Cl, Br, CN, —($C_1$-$C_4$)-alkyl, —O—($C_1$-$C_4$)-alkyl, —NH—($C_1$-$C_4$)-alkyl, —N(($C_1$-$C_4$)-alkyl)$_2$ or —CF$_3$, or R1 and R2 together with the ring atoms to which they are respectively attached form a ring, where the bicyclic ring system consisting of this ring and the pyridine ring carrying R1 and R2 is selected from the group consisting of quinoline and isoquinoline;

R3 and R4 together with the ring atoms to which they are respectively attached form a saturated or unsaturated 5-membered to 7-membered ring, where the ring consists only of carbon atoms or 1 or 2 of these atoms are replaced by O, S, SO, SO$_2$ or N—R5, selected from the group consisting of azepine, [1,2]diazepine, [1,3]diazepine, [1,4]diazepine, dihydroimidazolone, imidazole, imidazoline, imidazolidine, imidazolidinone, isothiazole, isothiazolidine, isothiazoline, isoxazole, isoxazoline, isoxazolidine, morpholine, oxathiazine dioxide, [1,2]oxazine, [1,3]oxazine, [1,4]oxazine, oxazolone, oxazole, oxazolidine, piperazine, piperidine, pyrazine, pyrazole, pyrazoline, pyrazolidine, pyridazine, pyridine, pyridinone, pyridopyrazines, pyridopyridines, pyrimidine, pyrrole, pyrrolidine, pyrrolidinone, pyrroline, 1,2,3,6-tetrahydropyridine, [1,2]thiazine, [1,3]thiazine, [1,4]thiazine, [1,3]thiazole, thiazole or thiazolidine, where the ring is unsubstituted or mono-, di- or trisubstituted independently of one another by F, Cl, —OH, —($C_1$-$C_4$)-alkyl, —O—($C_1$-$C_4$)-alkyl, C(O)—O—($C_1$-$C_4$)-alkyl, aryl or hetaryl;

X is N—R6 or O;
Y is C(O), CH$_2$ or CH—CH$_3$;
R5 is hydrogen, C(O)—($C_1$-$C_4$)-alkyl, C(O)—O—($C_1$-$C_4$)-alkyl, —($C_1$-$C_6$)-alkyl, aryl or hetaryl;
R6 is hydrogen, —($C_1$-$C_6$)-alkyl, —($C_3$-$C_7$)-cycloalkyl or —($C_1$-$C_4$)-alkylene-aryl;

where the term "hetaryl" means ring systems having 4 to 15 carbon atoms which are present in one, two or three ring systems connected together, and which comprise, depending on the ring size, one, two, three or four identical or different heteroatoms from the group consisting of oxygen, nitrogen and sulfur.

The invention furthermore relates to a compound of the formula I, and/or all stereoisomeric or tautomeric forms of the compound of the formula I and/or mixtures of these forms in any ratio, and/or a physiologically acceptable salt of the compound of the formula I, where R1 and R2 are identical or different and are independently of one another hydrogen, —($C_1$-$C_4$)-alkyl, —O—($C_1$-$C_4$)-alkyl, Br, F, Cl, aryl or hetaryl, where hetaryl is selected from the group consisting of acridinyl, azepinyl, azetidinyl, aziridinyl, benzimidazolyl, benzofuranyl, benzothiofuranyl, benzothiophenyl, benzoxazolyl, benzthiazolyl, benztriazolyl, benzisoxazolyl, benzisothiazolyl, carbazolyl, 4aH-carbazolyl, carbolinyl, quinazolinyl, quinolinyl, 4H-quinolizinyl, quinoxalinyl, quinuclidinyl, chromanyl, chromenyl, cinnolinyl, deca-hydroquinolinyl, dibenzofuranyl, dibenzothiophenyl, dihydrofuran[2,3-b]-tetrahydrofuranyl, dihydrofuranyl, dioxolyl, dioxanyl, 2H,6H-1,5,2-dithiazinyl, furanyl, furazanyl, imidazolidinyl, imidazolinyl, imidazolyl, 1H-indazolyl, indolinyl, indolizinyl, indolyl, 3H-indolyl, isobenzofuranyl, isoquinolinyl, isochromanyl, isoindazolyl, isoindolinyl, isoindolyl, isothiazolidinyl, 2-isothiazolinyl, isothiazolyl, isoxazolyl, isoxazolidinyl, 2-isoxazolinyl, morpholinyl, naphthyridinyl, octahydroisoquinolinyl, 1,2,3-oxadiazolyl, 1,2,4-oxadiazolyl, 1,2,5-oxadiazolyl, 1,3,4-oxadiazolyl, oxazolidinyl, oxazolyl, oxothiolanyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pryidooxazolyl, pyridoimidazolyl, pyridothiazolyl, pyridothiophenyl, pyridyl, pyrimidinyl, pyrrolidinyl, pyrrolinyl, 2H-pyrrolyl, pyrrolyl, tetrahydrofuranyl, tetrahydroisoquinolinyl, tetrahydroquinolinyl, tetrahydropyridinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolidinyl, thiazolinyl, thiazolyl, thienyl, thienoimidazolyl, thienooxazolyl, thienopyrrolyl, thienopyridinyl, thienothiazolyl, thienothiophenyl, thiomorpholinyl, triazinyl, 1,2,3-triazolyl, 1,2,4-triazolyl, 1,2,5-triazolyl, 1,3,4-triazolyl and xanthenyl, where alkyl, aryl and hetaryl are in each case unsubstituted or mono-, di- or trisubstituted independently of one another by F, Cl, CN, —($C_1$-$C_4$)-alkyl, —O—($C_1$-$C_4$)-alkyl, —N(($C_1$-$C_4$)-alkyl)$_2$ or —$CF_3$;

R3 and R4 together with the ring atoms to which they are respectively attached form a saturated or unsaturated 5-membered to 7-membered ring selected from the group consisting of azepine, [1,2]diazepine, [1,3]diazepine, [1,4]diazepine, dihydroimidazolone, imidazole, imidazoline, imidazolidine, imidazolidinone, isothiazole, isothiazolidine, isothiazoline, isoxazole, isoxazoline, isoxazolidine, morpholine, oxathiazine dioxide, [1,2]oxazine, [1,3]oxazine, [1,4]oxazine, oxazolone, oxazole, oxazolidine, piperazine, piperidine, pyrazine, pyrazole, pyrazoline, pyrazolidine, pyridazine, pyridine, pyridinone, pyrimidine, pyrrole, pyrrolidine, pyrrolidinone, pyrroline, 1,2,3,6-tetrahydropyridine, [1,2]thiazine, [1,3]thiazine, [1,4]thiazine, [1,3]thiazole, thiazole and thiazolidine, where the ring is unsubstituted or mono-, di- or trisubstituted independently of one another by F, Cl, —OH, —($C_1$-$C_4$)-alkyl, C(O)—O—($C_1$-$C_4$)-alkyl, aryl or hetaryl;

X is N—R6 or O;

Y is C(O), $CH_2$ or CH—$CH_3$;

R6 is hydrogen, —($C_1$-$C_6$)-alkyl, —($C_3$-$C_7$)-cycloalkyl or —($C_1$-$C_4$)-alkylene-aryl.

The invention furthermore relates to a compound of the formula I, and/or all stereoisomeric or tautomeric forms of the compound of the formula I and/or mixtures of these forms in any ratio, and/or a physiologically acceptable salt of the compound of the formula I, where R1 and R2 are identical or different and are independently of one another hydrogen, —($C_1$-$C_4$)-alkyl, Br, thienyl or phenyl, where thienyl and phenyl are in each case unsubstituted or mono- or disubstituted independently of one another by F, Cl, —O-methyl or —$CF_3$;

R3 and R4 together with the ring atoms to which they are respectively attached form a saturated or unsaturated 5-membered to 6-membered ring selected from the group consisting of azepine, [1,2]diazepine, [1,3]diazepine, [1,4]diazepine, dihydroimidazolone, imidazole, imidazoline, imidazolidine, imidazolidinone, isothiazole, isothiazolidine, isothiazoline, isoxazole, isoxazoline, isoxazolidine, morpholine, oxathiazine dioxide, [1,2]oxazine, [1,3]oxazine, [1,4]oxazine, oxazolone, oxazole, oxazolidine, piperazine, piperidine, pyrazine, pyrazole, pyrazoline, pyrazolidine, pyridazine, pyridine, pyridinone, pyrimidine, pyrrole, pyrrolidine, pyrrolidinone, pyrroline, 1,2,3,6-tetrahydropyridine, [1,2]thiazine, [1,3]thiazine, [1,4]thiazine, [1,3]thiazole, thiazole and thiazolidine, where the ring is unsubstituted or mono-, di- or trisubstituted independently of one another by F, —OH, C(O)—O—($C_1$-$C_4$)-alkyl, phenyl or hetaryl;

X is N—R6 or O;

Y is C(O), $CH_2$ or CH—$CH_3$;

R6 is hydrogen, —($C_1$-$C_6$)-alkyl, —($C_3$-$C_6$)-cycloalkyl or —($C_1$-$C_4$)-alkylene-phenyl.

The invention furthermore relates to a compound of the formula I, and/or all stereoisomeric or tautomeric forms of the compound of the formula I and/or mixtures of these forms in any ratio, and/or a physiologically acceptable salt of the compound of the formula I, where R1 and R2 are identical or different and are independently of one another hydrogen, —($C_1$-$C_4$)-alkyl, Br, thienyl or phenyl, where thienyl and phenyl are in each case unsubstituted or mono- or disubstituted independently of one another by F, Cl, —O-methyl or —$CF_3$;

R3 and R4 together with the ring atoms to which they are respectively attached form a saturated or unsaturated 5-membered to 6-membered ring selected from the group consisting of morpholine, piperazine, piperidine, pyrrolidine, 1,2,3,6-tetrahydropyridine and [1,3]thiazole, where the ring is unsubstituted or mono-, di- or trisubstituted independently of one another by F, —OH, phenyl or C(O)—O—($C_1$-$C_4$)-alkyl;

X is N—R6;

Y is C(O), $CH_2$ or CH—$CH_3$;

R6 is hydrogen, —($C_1$-$C_6$)-alkyl, cyclopropyl or —($C_1$-$C_4$)-alkylene-phenyl.

The invention furthermore relates to a compound of the formula I, and/or all stereoisomeric or tautomeric forms of the compound of the formula I and/or mixtures of these forms in any ratio, and/or a physiologically acceptable salt of the compound of the formula I, selected from the following compounds:

4-{(E)-2-[5-(3-fluorophenyl)pyridin-2-yl]vinyl}-2-methyloctahydropyrrolo[3,4-a]-indolizine-1,3-dione, 4-{(E)-2-[5-(3-fluorophenyl)pyridin-2-yl]vinyl}-2-methyloctahydropyrrolo[3,4-a]-indolizine-1,3-dione, 4-[(E)-2-(5-bromopyridin-2-yl)vinyl]-2-methyloctahydropyrrolo[3,4-a]indolizine-1,3-dione, 7-hydroxy-2-methyl-4-[(E)-2-(6-methylpyridin-2-yl)vinyl]hexahydropyrrolo[3,4-a]-pyrrolizine-1,3-dione, 2-methyl-4-[(E)-2-(6-methylpyridin-2-yl)vinyl]octahydropyrrolo[3,4-a]indolizine-1,3-dione, 2-methyl-4-[(E)-2-(6-methylpyridin-2-yl)vinyl]hexahydropyrrolo[3,4-a]pyrrolizine-1,3-dione, tert-butyl (8-{(E)-2-[5-(3-fluorophenyl)pyridin-2-yl]vinyl}-2-methyl-1,3-dioxodecahydro-2,5,7a-triazacyclopenta[a]indene-5-carboxylate, (S)-4-{(E)-2-[5-(3-fluorophenyl)pyridin-2-yl]vinyl}-7-hydroxy-2-methylhexahydropyrrolo[3,4-a]pyrrolizine-1,3-dione, (R)-4-{(E)-2-[5-(3-fluorophenyl)pyridin-2-yl]vinyl}-7-hydroxy-2-methylhexahydropyrrolo[3,4-a]pyrrolizine-1,3-dione, 6-{(E)-2-[5-(3-fluorophenyl)pyridin-2-yl]vinyl}-8-methylhexahydropyrrolo[3',4':3,4]-pyrrolo[2,1-c][1,4]oxazine-7,9-dione, 2-ethyl-4-{(E)-2-[5-(3-fluorophenyl)pyridin-2-yl]vinyl}octahydropyrrolo[3,4-a]indolizine-1,3-dione, 4-{(E)-2-[5-(3-fluorophenyl)pyridin-2-yl]vinyl}-2-methylhexahydropyrrolo[3,4-a]-pyrrolizine-1,3-dione, 5-{(E)-2-[5-(3-fluorophenyl)pyridin-2-yl]vinyl}-7-methyltetrahydropyrrolo[3',4':3,4]-pyrrolo[1,2-c]thiazole-6,8-dione,
2-methyl-4-{(E)-2-[5-(3-trifluoromethyl-phenyl)pyridin-2-yl]vinyl}octahydropyrrolo[3,4-a]indolizine-1,3-dione,
2-methyl-4-{(E)-2-[5-(3-trifluoromethyl-phenyl)pyridin-2-yl]vinyl}octahydropyrrolo[3,4-a]indolizine-1,3-dione,
4-{(E)-2-[5-(2-methoxyphenyl)pyridin-2-yl]vinyl}-2-methyloctahydropyrrolo[3,4-a]-indolizine-1,3-dione,
4-{(E)-2-[5-(2-chlorophenyl)pyridin-2-yl]vinyl}-2-methyloctahydropyrrolo[3,4-a]-indolizine-1,3-dione,
2-methyl-4-[(E)-2-(5-thiophen-3-ylpyridin-2-yl)vinyl]octahydropyrrolo[3,4-a]indolizine-1,3-dione,
4-{(E)-2-[5-(3-fluorophenyl)pyridin-2-yl]vinyl}-2-methyl-3a,4,6,9,9a,9b-hexahydropyrrolo[3,4-a]indolizine-1,3-dione,
2-cyclopropyl-4-{(E)-2-[5-(3-fluorophenyl)pyridin-2-yl]vinyl}octahydropyrrolo[3,4-a]-indolizine-1,3-dione, and
8-{(E)-2-[5-(3-fluorophenyl)pyridin-2-yl]vinyl}-2-methyloctahydro-2,5,7a-triazacyclopenta[a]indene-1,3-dione.

The terms "alkyl", "—($C_1$-$C_6$)-alkyl" and "—($C_1$-$C_4$)-alkyl" mean hydrocarbon radicals whose carbon chain is straight-chain or branched and which comprise 1, 2, 3, 4, 5 or 6 carbon atoms and 1, 2, 3 or 4 carbon atoms, respectively, for example methyl, ethyl, propyl, isopropyl, butyl, isobutyl, sec-butyl, tert-butyl, pentyl, isopentyl, neopentyl, 1-ethylpropyl, hexyl, 2,3-dimethylbutyl or neohexyl. Preferably, —($C_1$-$C_6$)-alkyl comprises 1 to 4 carbon atoms.

The terms "—O-alkyl", "—O—($C_1$-$C_6$)-alkyl" and "—O—($C_1$-$C_4$)-alkyl" mean alkoxy radicals whose carbon chain is straight-chain or branched and which comprise 1, 2, 3, 4, 5 or 6 carbon atoms and 1, 2, 3 or 4 carbon atoms, respectively, such as methoxy, ethoxy, propoxy, isopropoxy, butoxy, isobutoxy, tert-butoxy, 1-pentoxy, 2-pentoxy, 3-pentoxy, 1-hexoxy, 2-hexoxy or 3-hexoxy. Preferably, —O—($C_1$-$C_6$)-alkyl comprises 1 to 4 carbon atoms.

The term "—($C_3$-$C_7$)-cycloalkyl" means 3- to 7-membered monocycles such as cyclopropyl, cyclobutyl, cyclopentyl, cyclohexyl or cycloheptyl; the term "—($C_3$-$C_6$)-cycloalkyl" means 3- to 6-membered monocycles such as cyclopropyl, cyclobutyl, cyclopentyl or cyclohexyl.

The term "aryl" means aromatic carbon radicals having 6 to 14 carbon atoms in the ring. Examples of aryl radicals are phenyl, naphthyl, for example 1-naphthyl, 2-naphthyl, anthryl or fluorenyl. Phenyl radicals and naphthyl radicals, in particular phenyl radicals, are preferred aryl radicals.

The term "hetaryl" means ring systems having 4 to 15 carbon atoms which are present in one, two or three ring systems connected together and which comprise, depending on the ring size, one, two, three or four identical or different heteroatoms from the group consisting of oxygen, nitrogen or sulfur. Examples of these ring systems are the radicals acridinyl, azepinyl, azetidinyl, aziridinyl, benzimidazolyl, benzofuranyl, benzothiofuranyl, benzothiophenyl, benzoxazolyl, benzthiazolyl, benztriazolyl, benzisoxazolyl, benzisothiazolyl, carbazolyl, 4aH-carbazolyl, carbolinyl, quinazolinyl, quinolinyl, 4H-quinolizinyl, quinoxalinyl, quinuclidinyl, chromanyl, chromenyl, cinnolinyl, deca-hydroquinolinyl, dibenzofuranyl, dibenzothiophenyl, dihydrofuran[2,3-b]-tetrahydrofuranyl, dihydrofuranyl, dioxolyl, dioxanyl, 2H,6H-1,5,2-dithiazinyl, furanyl, furazanyl, imidazolidinyl, imidazolinyl, imidazolyl, 1H-indazolyl, indolinyl, indolizinyl, indolyl, 3H-indolyl, isobenzofuranyl, isoquinolinyl, isochromanyl, isoindazolyl, isoindolinyl, isoindolyl, isothiazolidinyl, 2-isothiazolinyl, isothiazolyl, isoxazolyl, isoxazolidinyl, 2-isoxazolinyl, morpholinyl, naphthyridinyl, octahydroisoquinolinyl, 1,2,3-oxadiazolyl, 1,2,4-oxadiazolyl, 1,2,5-oxadiazolyl, 1,3,4-oxadiazolyl, oxazolidinyl, oxazolyl, oxothiolanyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pryidooxazolyl, pyridoimidazolyl, pyridothiazolyl, pyridothiophenyl, pyridyl, pyrimidinyl, pyrrolidinyl, pyrrolinyl, 2H-pyrrolyl, pyrrolyl, tetrahydrofuranyl, tetrahydroisoquinolinyl, tetrahydroquinolinyl, tetrahydropyridinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolidinyl, thiazolinyl, thiazolyl, thienyl, thienoimidazolyl, thienooxazolyl, thienopyrrolyl, thienopyridinyl, thienothiazolyl, thienothiophenyl, thiomorpholinyl, triazinyl, 1,2,3-triazolyl, 1,2,4-triazolyl, 1,2,5-triazolyl, 1,3,4-triazolyl or xanthenyl.

The term "R3 and R4 together with the ring atoms to which they are respectively attached form a saturated or unsaturated 5-membered to 7-membered ring, where the ring consists only of carbon atoms or 1 or 2 of these atoms are replaced by O, S, SO, $SO_2$ or N—R5" means ring systems such as azepine, [1,2]diazepine, [1,3]diazepine, [1,4]diazepine, dihydroimidazolone, imidazole, imidazoline, imidazolidine, imidazolidinone, isothiazole, isothiazolidine, isothiazoline, isoxazole, isoxazoline, isoxazolidine, morpholine, oxathiazine dioxide, [1,2]oxazine, [1,3]oxazine, [1,4]oxazine, oxazolone, oxazole, oxazolidine, piperazine, piperidine, pyrazine, pyrazole, pyrazoline, pyrazolidine, pyridazine, pyridine, pyridinone, pyridopyrazines, pyridopyridines, pyrimidine, pyrrole, pyrrolidine, pyrrolidinone, pyrroline, 1,2,3,6-tetrahydropyridine, [1,2]thiazine, [1,3]thiazine, [1,4]thiazine, [1,3]thiazole, thiazole, thiazoline or thiazolidine.

The term "R1 and R2 together with the ring atoms to which they are respectively attached form a 5-membered to 6-membered ring, where the ring consists only of carbon atoms, or 1, 2 or 3 of these atoms are replaced by nitrogen, oxygen or sulfur atoms" means, for example, the following bicyclic ring systems consisting of this ring and the pyridine ring which carries R1 and R2: quinoline, 6,7-dihydro-5H-[1]pyridine, [1,3]dioxolo[4,5-b]pyridine, furo[3,2-b]pyridine, isoquinoline, [1,7]naphthyridine, pyridopyrazines, pyrido[2,3-c]pyridazine, pyridopyridines, pyrido[2,3-d]pyrimidine, 5H-[1]pyridine, 1H-pyrrolo[2,3-b]pyridine, 5,6,7,8-tetrahydroquinoline or thieno[3,2-b]pyridine.

The term "halogen" means fluorine, chlorine, bromine or iodine, preferably fluorine, chlorine, or bromine, in particular fluorine or chlorine.

The term "X is O", that is "X is oxygen or an oxygen atom", means the following component ring of the formula I:

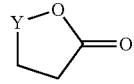

The term "X is N—R6" means the following component ring of the formula I:

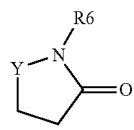

The term "Y is C(O)" means the following component ring of the formula I:

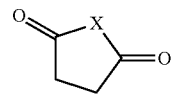

The term "Y is CH$_2$" means the following component ring of the formula I:

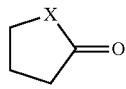

The term "Y is CH—CH$_3$" means the following component ring of the formula I:

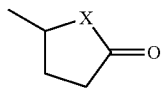

The term "Y is C(CH$_3$)$_2$" means the following component ring of the formula I:

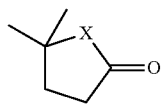

Functional groups in the compounds of the formula I and the intermediates used for their preparation, for example amino or carboxyl groups, can be masked by suitable protective groups. Suitable protective groups for amino functions are for example the tert-butoxycarbonyl, the benzyloxycarbonyl or the phthaloyl group and the trityl or tosyl protective group. Suitable protective groups for the carboxyl function are for example alkyl, aryl or arylalkyl esters. Protective groups can be introduced and removed by techniques which are well known or described herein (see Greene, T. W., Wuts, P. G. M., Protective Groups in Organic Synthesis (1999), 3rd Ed., Wiley-Interscience, or Kocienski, P. J., Protecting Groups (2004), 3rd Ed., Thieme). The term protective group may also include corresponding polymer-bound protective groups.

In one embodiment of the invention, R1 and R2 are identical or different and are independently of one another hydrogen, —(C$_1$-C$_6$)-alkyl, —O—(C$_1$-C$_6$)-alkyl, aryl, halogen or hetaryl, where alkyl, aryl and hetaryl are in each case unsubstituted or mono-, di- or trisubstituted independently of one another by F, Cl, Br, CN, —(C$_1$-C$_4$)-alkyl, —O—(C$_1$-C$_4$)-alkyl, —NH—(C$_1$-C$_4$)-alkyl, —N((C$_1$-C$_4$)-alkyl)$_2$, —NH$_2$, —OH, —O—CF$_3$, —S—CF$_3$ or —CF$_3$. In another embodiment, R1 and R2 are identical or different and are independently of one another hydrogen, —(C$_1$-C$_6$)-alkyl, —O—(C$_1$-C$_6$)-alkyl, aryl, halogen or hetaryl, where aryl and hetaryl are in each case unsubstituted or mono-, di- or trisubstituted independently of one another by F, Cl, Br, CN, —(C$_1$-C$_4$)-alkyl, —O—(C$_1$-C$_4$)-alkyl, —NH—(C$_1$-C$_4$)-alkyl, —N((C$_1$-C$_4$)-alkyl)$_2$, —NH$_2$, —OH, —O—CF$_3$, —S—CF$_3$ or —CF$_3$. In another embodiment, R1 and R2 are identical or different and are independently of one another hydrogen, —(C$_1$-C$_6$)-alkyl, —O—(C$_1$-C$_6$)-alkyl, aryl, halogen or hetaryl, where aryl and hetaryl are in each case unsubstituted or mono-, di- or trisubstituted independently of one another by F, Cl, Br, —(C$_1$-C$_4$)-alkyl, —O—(C$_1$-C$_4$)-alkyl, —O—CF$_3$ or —CF$_3$. In another embodiment, R1 and R2 are identical or different and are independently of one another hydrogen, —(C$_1$-C$_6$)-alkyl, aryl, halogen or hetaryl, where aryl and hetaryl are in each case unsubstituted or mono-, di- or trisubstituted independently of one another by F, Cl, Br, —(C$_1$-C$_4$)-alkyl, —O—(C$_1$-C$_4$)-alkyl, —O—CF$_3$ or —CF$_3$. In another embodiment, R1 and R2 are identical or different and are independently of one another hydrogen, —(C$_1$-C$_6$)-alkyl, aryl, halogen or hetaryl, where aryl and hetaryl are in each case unsubstituted or mono-, di- or trisubstituted independently of one another by F, Cl, Br or —(C$_1$-C$_4$)-alkyl.

In one embodiment of the invention, one of the groups R1 and R2 is hydrogen, —(C$_1$-C$_6$)-alkyl, —O—(C$_1$-C$_6$)-alkyl or halogen, in another embodiment it is hydrogen, —(C$_1$-C$_6$)-alkyl or halogen, in another embodiment it is hydrogen or halogen, and in one embodiment the other group R1 or R2 is —(C$_1$-C$_6$)-alkyl, —O—(C$_1$-C$_6$)-alkyl, aryl or hetaryl, in another embodiment, it is —(C$_1$-C$_6$)-alkyl, aryl or hetaryl, in another embodiment, it is aryl or hetaryl, in another embodiment, it is phenyl, where in one embodiment the alkyl, —O-alkyl, aryl, phenyl or hetaryl representing the other group R1 or R2 is in each case unsubstituted or mono-, di- or trisubstituted independently of one another by F, Cl, Br, CN, —(C$_1$-C$_4$)-alkyl, —O—(C$_1$-C$_4$)-alkyl, —OH, —NH$_2$, —NH—(C$_1$-C$_4$)-alkyl, —N((C$_1$-C$_4$)-alkyl)$_2$, —OCF$_3$, —SCF$_3$ or —CF$_3$, in another embodiment unsubstituted or mono-, di- or trisubstituted independently of one another by F, Cl, Br, —(C$_1$-C$_4$)-alkyl, —O—(C$_1$-C$_4$)-alkyl, —OCF$_3$ or —CF$_3$, in another embodiment unsubstituted or mono-, di- or trisubstituted independently of one another by F, Cl, Br or —(C$_1$-C$_4$)-alkyl.

In one embodiment of the invention, aryl which represents R1 or R2 is phenyl, and in another embodiment hetaryl which represents R1 or R2 is thienyl, where phenyl and thienyl can be unsubstituted or substituted as indicated. In one embodiment of the invention, substituted groups representing R1 or R2 are substituted by one or two of the substituents indicated, which may be identical or different.

In one embodiment of the invention, the ring formed by R3 and R4 together with the ring atoms to which they are respectively attached is saturated or contains one or two double bonds in the ring, in another embodiment it is saturated or contains one double bond in the ring, in another embodiment it is saturated, in another embodiment it contains one double bond in the ring. In one embodiment, the ring formed by R3 and R4 together with the ring atoms to which they are respectively attached is a 5-membered to 6-membered ring, in another embodiment, it is a 5-membered ring, in another embodiment it is a 6-membered ring. In one embodiment, the ring formed by R3 and R4 together with the ring atoms to which they are respectively attached consists only of carbon atoms, except for the nitrogen atom which carries the group R3, or one of the ring carbon atoms is replaced by O, S, SO, SO$_2$ or N—R5, in another embodiment, the ring formed by R3 and R4 together with the ring atoms to which they are respectively attached consists only of carbon atoms, except for the nitrogen atom which carries the group R3. If more than one ring heteroatom, including the nitrogen atom which carries the group R3, is present in the ring which is formed by R3 and R4 together with the ring atoms to which they are respectively attached, in one embodiment of the invention two ring heteroatoms are not in adjacent ring positions. If ring carbon atoms are replaced by O, S, SO, SO$_2$ or N—R5, in one embodiment they are replaced by O, S or N—R5, in another embodiment by O or S, in another embodiment by 0, in another embodiment by S, in another embodiment by S, SO or SO$_2$, in another embodiment by N—R5. In one embodiment, the ring formed by R3 and R4 together with the ring atoms to which they are respectively attached is a pyrrolidine ring, piperidine ring, tetrahydropyridine ring, thiazolidine ring, oxazolidine ring, thiomorpholine ring, morpholine ring or piperazine ring, in another embodiment a pyrrolidine ring, piperidine ring, thiazolidine ring, oxazolidine ring, thiomorpholine ring, morpholine ring or piperazine ring, in another embodiment a pyrrolidine ring, piperidine ring, thiazolidine ring, morpholine ring or piperazine ring, in another embodiment a pyrrolidine ring, piperidine ring, thiazolidine ring or morpholine ring, in another embodiment a pyrrolidine ring or piperidine ring, all of which may be unsubstituted or substituted as indicated.

In one embodiment, the ring which is formed by R3 and R4 together with the ring atoms to which they are respectively attached is unsubstituted or mono-, di- or trisubstituted independently of one another by F, Cl, —OH, —NH—R7, —($C_1$-$C_4$)-alkyl, —O—($C_1$-$C_4$)-alkyl or —C(O)—O—($C_1$-$C_4$)-alkyl, in another embodiment it is unsubstituted or mono-, di- or trisubstituted independently of one another by F, Cl, —OH, —($C_1$-$C_4$)-alkyl, —O—($C_1$-$C_4$)-alkyl or —C(O)—O—($C_1$-$C_4$)-alkyl, in another embodiment it is unsubstituted or mono-, di- or trisubstituted independently of one another by F, —OH, —($C_1$-$C_4$)-alkyl or —O—($C_1$-$C_4$)-alkyl, in another embodiment it is unsubstituted or mono-, di- or trisubstituted independently of one another by F, —OH, —($C_1$-$C_4$)-alkyl or —C(O)—O—($C_1$-$C_4$)-alkyl.

In one embodiment of the invention, X is N—R6, in another embodiment it is O.

In one embodiment of the invention, Y is C(O), $CH_2$ or $C(CH_3)_2$, in another embodiment it is C(O) or $C(CH_3)_2$, in another embodiment it is C(O), in another embodiment it is $CH_2$ or $C(CH_3)_2$.

In one embodiment of the invention, R5 is hydrogen, —C(O)—($C_1$-$C_4$)-alkyl, —C(O)—O—($C_1$-$C_4$)-alkyl, —($C_1$-$C_6$)-alkyl, —($C_2$-$C_4$)-alkyl-O—($C_1$-$C_4$)-alkyl or —($C_2$-$C_4$)-alkyl-OH, in another embodiment it is hydrogen, —C(O)—($C_1$-$C_4$)-alkyl, —C(O)—O—($C_1$-$C_4$)-alkyl or —($C_1$-$C_6$)-alkyl, in another embodiment it is hydrogen, —C(O)—O—($C_1$-$C_4$)-alkyl or —($C_1$-$C_6$)-alkyl, in another embodiment it is hydrogen or —C(O)—O—($C_1$-$C_4$)-alkyl.

In one embodiment of the invention, R7 is hydrogen, —C(O)—($C_1$-$C_4$)-alkyl, —C(O)—O—($C_1$-$C_4$)-alkyl or —($C_1$-$C_6$)-alkyl, in another embodiment it is hydrogen, —C(O)—($C_1$-$C_4$)-alkyl or —C(O)—O—($C_1$-$C_4$)-alkyl, in another embodiment it is hydrogen or —($C_1$-$C_6$)-alkyl.

In one embodiment of the invention, R6 is hydrogen, —($C_1$-$C_6$)-alkyl, —($C_3$-$C_7$)-cycloalkyl or C(O)—O—($C_1$-$C_4$)-alkyl, in another embodiment it is hydrogen, —($C_1$-$C_6$)-alkyl, —($C_3$-$C_7$)-cycloalkyl or —($C_1$-$C_4$)-alkylene-aryl, in another embodiment it is —($C_1$-$C_6$)-alkyl, —($C_3$-$C_7$)-cycloalkyl or —($C_1$-$C_4$)-alkylene-aryl, in another embodiment it is —($C_1$-$C_6$)-alkyl or —($C_3$-$C_7$)-cycloalkyl, in another embodiment it is —($C_1$-$C_6$)-alkyl. In one embodiment, —($C_3$-$C_7$)-cycloalkyl which represents R6 is cyclopropyl, cyclobutyl, cyclopentyl or cyclohexyl, in another embodiment it is cyclopropyl, cyclobutyl or cyclopentyl, in another embodiment it is cyclopropyl or cyclobutyl, in another embodiment it is cyclopropyl.

The invention relates to all combinations of definitions of the compounds of the formula I and one or more of the embodiments described, and also to all combinations of definitions of the compounds of the formula I and one or more of the embodiments described and/or one or more of the specific meanings described which a group in the compounds of the formula I may have.

The compounds of the invention can be prepared by well known processes or by processes described herein. The invention also relates to a process for preparing a compound of the formula I and/or a stereoisomeric or tautomeric form of the compound of the formula I and/or a physiologically tolerated salt of the compound of the formula I which allows the preparation of the compounds of the formula I, their stereoisomeric or tautomeric forms or their physiologically acceptable salts and which comprises a) reacting a compound of the formula II,

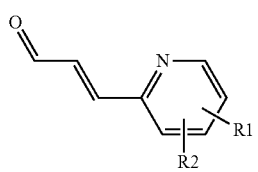

II where the radicals R1 and R2 are as defined in formula I, with a compound of the formula III and a compound of the formula IV,

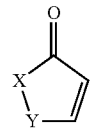

III

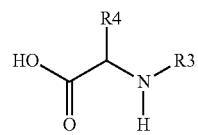

IV where the radicals X, Y, R3 and R4 are as defined in formula I, in the presence of a solvent at 20° C. to 120° C. to give a compound of the formula I; or b) reacting a compound of the formula V,

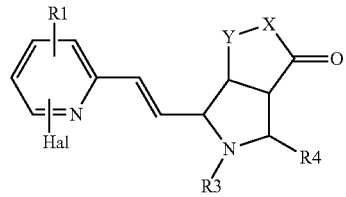

V where the radicals X, Y, R1, R3 and R4 are as defined in formula I and Hal has the meaning of chlorine, bromine, iodine or triflate (trifluoromethanesulfonyloxy), with a compound of the formula R2-B(OH)$_2$ or a derivative thereof in the presence of a base and of a suitable metal catalyst in a suitable solvent or solvent mixture to give a compound of the formula I; or c) reacting a compound of the formula I in which X has the meaning of NH with a suitable alkylating agent in the presence of a base and in a suitable inert solvent at room temperature or at elevated temperature to give a compound of the formula I in which X has the meaning of N—R6 and R6 is —($C_1$-$C_6$)-alkyl, —($C_3$-$C_7$)-cycloalkyl or —($C_1$-$C_4$)-alkylene-aryl; or d) fractionating the compound of the formula I which has been prepared by processes a) to c), or a suitable precursor of the formula I which, owing to its chemical structure, occurs in enantiomeric or diastereomeric forms, by salt formation with enantiomerically pure acids or bases, chromatography on chiral stationary phases or derivatization by means of chiral enantiomerically pure compounds such as amino acids, separation of the diastereomers obtained in this way, and elimination of the chiral auxiliary groups, into the pure enantiomers or diastereomers; or e) either isolating the compound of the formula I prepared by processes a) to d) in free form or liberating it from non-physiologically acceptable salts or, in the case where acidic or basic groups are present, converting it into a physiologically acceptable salt.

The compounds of the formula II can be prepared by reacting an aldehyde of the formula VI with a compound of the formula VII

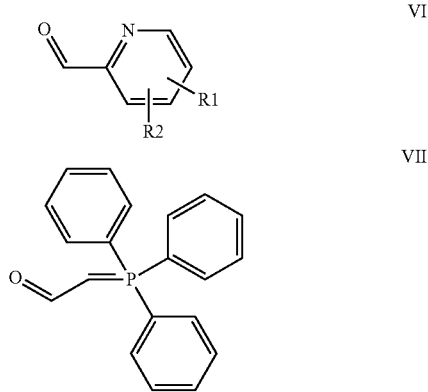

or another suitable phosphorus ylide reagent in a suitable solvent and, where appropriate, at elevated temperature. Aldehydes of the formula VI are either commercially available or can be prepared by known processes. Thus, for example, halogen-substituted pyridinealdehydes can be reacted in the presence of suitable transition metal catalysts such as palladium or nickel and their phosphane complexes with boric acid derivatives to give alkyl-, aryl- and hetaryl-substituted derivatives of the formula VI.

Acidic or basic compounds of the formula I may be in the form of their salts or in free form. Pharmacologically acceptable salts are preferred, in particular pharmaceutically acceptable salts, for example alkali metal or alkaline earth metal salts or hydrochlorides, sulfates, hemisulfates, methylsulfonates, p-toluenesulfonates, all possible phosphates, and salts of amino acids, natural bases or carboxylic acids such as lactates, citrates, tartrates, acetates, adipates, fumarates, gluconates, glutamates, maleates or palmoates. Physiologically acceptable salts are prepared from compounds of the formula I capable of salt formation, including their stereoisomeric forms, in process step c) in a manner known per se. If compounds of the formula I contain acidic functionality, stable alkali metal, alkaline earth metal or optionally substituted ammonium salts can be formed with basic reagents such as hydroxides, carbonates, bicarbonates, alcoholates, and ammonia or organic bases, for example trimethyl- or triethylamine, ethanolamine, diethanolamine or triethanolamine, trometamol or else basic amino acids, for instance lysine, ornithine or arginine. Basic groups of the compounds of the formula I form acid addition salts with acids. Suitable for this purpose are both inorganic and organic acids such as hydrochloric or hydrobromic, sulfuric, hemisulfuric, phosphoric, methanesulfonic, benzenesulfonic, p-toluenesulfonic, 4-bromobenzenesulfonic, cyclohexylamidosulfonic, trifluoromethylsulfonic, 2-hydroxyethanesulfonic, acetic, oxalic, tartaric, succinic, glycerolphosphoric, lactic, malic, adipinic, citric, fumaric, maleic, gluconic, glucuronic, palmitic or trifluoroacetic acid.

The compounds of the formula I may contain two or more asymmetric carbon atoms and occur in the form of diastereomers or enantiomers or mixtures thereof. If the compound of the formula I occurs as a mixture of diastereomers or enantiomers or results as a mixture thereof in the chosen synthesis, it can be separated into the pure stereoisomers either by chromatography on an optionally chiral support material or, if the racemic compound of the formula I is capable of salt formation, it is also possible to carry out a fractional crystallization of the diastereomeric salts formed with an optically active base or acid as auxiliary. Examples of suitable chiral stationary phases for thin-layer or column chromatographic separation of enantiomers are modified silica gel supports (called Pirkle phases) and high molecular weight carbohydrates such as triacetylcellulose. For analytical purposes it is also possible to use gas chromatographic methods on chiral stationary phases after appropriate derivatization known to the skilled worker. To separate enantiomers of the racemic carboxylic acids, the diastereomeric salts of differing solubility are formed with an optically active, usually commercially available, base such as (−)-nicotine, (+)- and (−)-phenylethylamine, quinine bases, L-lysine or L- and D-arginine, the less soluble component is isolated as solid, the more soluble diastereomer is deposited from the mother liquor, and the pure enantiomers are obtained from the diastereomeric salts obtained in this way. It is possible in the same way in principle to convert the racemic compounds of the formula I which contain a basic group such as an amino group, with optically active acids such as (+)-camphor-10-sulfonic acid, D- and L-tartaric acid, D- and L-lactic acid, and (+)- and (−)-mandelic acid, into the pure enantiomers. It is also possible to convert chiral compounds containing alcohol or amine functions with appropriately activated or, where appropriate, N-protected enantiomerically pure amino acids into the corresponding esters or amides, or conversely chiral carboxylic acids with carboxy-protected enantiomerically pure amino acids into the amides or with enantiomerically pure hydroxy carboxylic acids such as lactic acid into the corresponding chiral esters. The chirality of the amino acid or alcohol residue which has been introduced in enantiomerically pure form can then be utilized to separate the isomers by carrying out a separation of the diastereomers which are now available by crystallization or chromatography on suitable stationary phases, and then eliminating the included chiral moiety again by suitable methods.

A further possibility with some of the compounds of the invention is to prepare the framework structures from diastereomerically or enantiomerically pure starting materials. It is thus possible also to employ other or simplified processes for purifying the final products. These starting materials have previously been prepared enantiomerically or diastereomerically pure by processes known from the literature. This may mean in particular that either enantioselective processes are employed in the synthesis of the basic structures, or else a separation of enantiomers or diastereomers is carried out at an early stage of the synthesis and not at the stage of the final products. A simplification of these separations can likewise be achieved by proceeding in two or more stages.

The invention also relates to medicaments and pharmaceutical preparations having an effective content of at least one compound of the formula I and/or a physiologically tolerated salt of the compound of the formula I and/or a stereoisomeric or tautomeric form of the compound of the formula I, together with a pharmaceutically suitable and physiologically acceptable carrier, additive and/or other active compounds and auxiliaries. The invention furthermore relates to a compound of the formula I and/or all stereoisomeric or tautomeric forms of the compound of the formula I and/or mixtures of these forms in any ratio, and/or a physiologically acceptable salt of the compound of the formula I, for use as a pharmaceutic or active compound in a medicament.

By virtue of the pharmacological properties, the compounds of the invention are suitable for example for the prophylaxis, secondary prevention and therapy of all disorders which can be treated by inhibition of the protease-activated receptor 1 (PAR1). Thus, the compounds of the invention are suitable both for a prophylactic and a therapeutic use on humans. They are suitable both for acute treatment and for chronic treatment in long-term therapy. The compounds of the formula I can be employed in patients suffering from impairments of well being or diseases associated with thromboses, embolisms, hypercoagulability or fibrotic changes. These include myocardial infarction, angina pectoris and all other types of acute coronary syndrome, acute stroke or its secondary prevention, peripheral vascular disorders, deep vein thrombosis, pulmonary embolism, embolic or thrombotic events caused by cardiac arrhythmias, cardiovascular events such as restenosis following revascularization, angioplasty and similar procedures such as stent implantations and bypass operations.

The compounds of the formula I can further be employed in all procedures leading to contact of blood with foreign surfaces, such as for dialysis patients and patients with indwelling catheters. Compounds of the formula I can be employed in order to reduce the risk of thrombosis following surgical procedures such as knee and hip joint operations. Compounds of the formula I are suitable for the treatment of patients with disseminated intravascular coagulation, sepsis and other intravascular events associated with inflammation.

Compounds of the formula I are further suitable for the prophylaxis and treatment of patients with atherosclerosis, diabetes and the metabolic syndrome and the sequelae thereof. Impairments of the hemostatic system (for example fibrin deposits) have been implicated in mechanisms leading to tumor growth and tumor metastasis, and in inflammatory and degenerative articular disorders such as rheumatoid arthritis and arthrosis. Compounds of the formula I are suitable for retarding or preventing such processes.

Further indications for the use of the compounds of the formula I are fibrotic changes in the lung such as chronic obstructive pulmonary disease, adult respiratory distress syndrome (ARDS) and of the eye such as fibrin deposits following eye operations. Compounds of the formula I are also suitable for the prevention and/or treatment of scarring.

The medicaments of the invention can be administered for example by oral, inhalational, rectal or transdermal administration or by subcutaneous, intraarticular, intraperitoneal or intravenous injection. Oral administration is preferred. Coating of stents with compounds of the formula I and other surfaces which come into contact with blood in the body is possible.

The invention also relates to a process for manufacturing a medicament, which comprises making a suitable dosage form from at least one compound of the formula I with a pharmaceutically suitable and physiologically acceptable carrier and, where appropriate, further suitable active compounds, additives or auxiliaries.

Suitable solid or pharmaceutical formulations are, for example, granules, powder, coated tablets, tablets, (micro) capsules, suppositories, syrups, solutions, suspensions, emulsions, drops or injectable solutions, and products with protracted release of active compound, in the production of which customary aids such as carriers, disintegrants, binders, coating agents, swelling agents, glidants or lubricants, flavorings, sweeteners and solubilizers are used. Auxiliaries which are frequently used and which may be mentioned are magnesium carbonate, titanium dioxide, lactose, mannitol and other sugars, talc, milk protein, gelatin, starch, cellulose and its derivatives, animal and vegetable oils such as fish liver oil, sunflower, peanut or sesame oil, polyethylene glycol and solvents such as, for example, sterile water and monohydric or polyhydric alcohols such as glycerol.

The pharmaceutical products are preferably manufactured and administered in dosage units, where each unit comprises as active compound a particular dose of the compound of the invention of the formula I. In the case of solid dosage units such as tablets, capsules, coated tablets or suppositories, this dose can be up to about 1000 mg, but preferably about 50 mg to 300 mg and, in the case of injection solutions in ampoule form, up to about 300 mg but preferably about 10 mg to 100 mg.

The daily doses indicated for the treatment of an adult patient weighing about 70 kg are, depending on the activity of the compound of the formula I, from about 2 mg to 1000 mg of active compound, preferably about 50 mg to 500 mg. However, in some circumstances, higher or lower daily doses may also be appropriate. The daily dose can be administered either by a single administration in the form of a single dosage unit or else a plurality of smaller dosage units or by multiple administration of divided doses at particular intervals.

Compounds of the formula I can be administered both as monotherapy and in combination or together with all antithrombotics (anticoagulants and platelet aggregation inhibitors), thrombolytics (plasminogen activators of every type), other substances having profibrinolytic activity, antihypertensives, regulators of blood glucose, lipid-lowering agents and antiarrhythmics. Suitable platelet aggregation inhibitors in this connection are cyclooxygenase 1 inhibitors such as aspirin, irreversible $P2Y_{12}$ antagonists such as clopidogrel or prasugrel, reversible $P2Y_{12}$ antagonists such as cangrelor or AZD6140 and thromboxane $A_2$/prostaglandin $H_2$ antagonists such as terutroban. It has been possible to show additive effects of PAR1 blockade in combination with $P2Y_{12}$ blockade for example (M. Chintala et al., Eur. Heart J. 28 (Abstract Supplement 1): 188, 2007).

EXAMPLES

The prepared compounds were usually characterized by spectroscopic and chromatographic data, specifically mass spectra (MS) and HPLC retention times (Rt; in min), which were obtained by combined analytical HPLC/MS characterization (LC/MS). In the MS characterization, usually the mass number (m/z) of the peak of the molecular ion (M or M⁺) or of a related ion such as the ion M+1 (or M+1⁺; protonated molecular ion M+H⁺), which formed depending on the ionization method used, is indicated. The ionization method generally used was electrospray ionization (ESI). The following LC/MS methods were used:

Method D
   column: YMC J'sphere ODS H80 20×2.1 mm 4 μm
   solvent: MeCN:$H_2O$+0.05% TFA (flow rate 1 ml/min)
   gradient: from 4:96 (0 min) to 95:5 (2 min) to 95:5 (2.4 min) to 96:4 (2.45 min)
   ionization: ESI⁺

Method J column: Luna C18 10×2 mm 3 μm solvent: MeCN+0.05% TFA:H₂O+0.05% TFA (flow rate 1.1 ml/min)

gradient: 7:93 (0 min) to 95:5 (1.2 min) to 95:5 (1.4 min) to 7:93 (1.45 min)

ionization: ESI⁺

The compounds were further characterized by 1H NMR spectroscopy. The abbreviations used are either explained or correspond to usual conventions. Evaporation of solvents usually took place under reduced pressure at 35° C. to 45° C. in a rotary evaporator and is described as "freed of solvent", "concentrated", "evaporated" or "solvent removed". The reactions took place in standard reaction apparatuses such as one-neck or multineck flasks which, unless otherwise described, had volumes of from 5 ml to 2000 ml appropriate for requirements and were equipped with septum, stoppers, condenser, stirrer or other items of equipment as required. Unless mentioned otherwise, all the reactions took place under argon as protective gas and were stirred with magnetic stirrers.

Abbreviations Used:

Boc tert-butoxycarbonyl

DCM dichloromethane

DMSO dimethyl sulfoxide

MeCN acetonitrile

MeOH methanol

Rt retention time

RT room temperature (20° C. to 25° C.)

sat. saturated

TFA trifluoroacetic acid

A plurality of diastereomers is usually formed in the reactions and can be separated as racemic mixtures by column chromatography. Unless indicated, the assignment of these racemic mixtures to particular configurations is not yet unambiguous. Likewise, the absolute assignment of the pure diastereomers obtained from the racemic mixtures by chiral column chromatography has not yet been done. Where a defined stereochemistry is indicated, the assignment was derived from the coupling constants of the hydrogen atoms in the pyrrole ring by NMR spectroscopy methods.

Example 1

5-(3-Fluorophenyl)pyridine-2-carbaldehyde

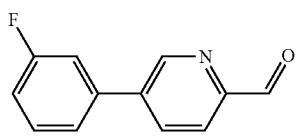

A mixture of 2 g of 5-bromopyridine-2-carbaldehyde, 1.96 g of 3-fluorophenylboronic acid, 11.2 g of K₂CO₃, 160 ml of toluene, 60 ml of water, 60 ml of ethanol and 0.93 mg of tetrakis(triphenylphosphine)palladium(0) is stirred at 100° C. under argon for 2 hours. The solvents are evaporated and the residue is dispersed in 100 ml of water, and the product is extracted with 2 portions of 30 ml of ethyl acetate. The organic phase is washed with 30 ml of sat. brine, dried over sodium sulfate and concentrated. The resulting residue is recrystallized from 28 ml of isopropanol.

Yield: 1.3 g, LC/MS (method D): m/z=202 (M+1); Rt=1.317 min

Example 2

(E)-3-[5-(3-Fluorophenyl)pyridin-2-yl]propenal

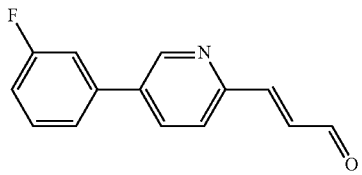 [SMILES: O=C/C=C/c1ccc(-c2cccc(F)c2)cn1]

584 mg of 5-(3-fluorophenyl)pyridine-2-carbaldehyde and 883 mg of (triphenylphosphoranylidene)acetaldehyde are stirred at RT overnight. The solvents are evaporated and the residue is purified by column chromatography (silica gel, MeOH:DCM=99.5:0.5).

Yield: 450 mg, LC/MS (method J): m/z=228 (M+1); Rt=0.887 min

Example 3

(E)-3-(5-Bromopyridin-2-yl)-propenal

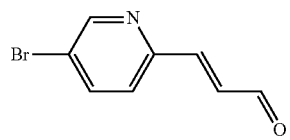 [SMILES: O=C/C=C/c1ccc(Br)cn1]

818 mg of (triphenylphosphoranylidene)acetaldehyde and 500 mg of 5-bromopyridine-2-carbaldehyde are stirred at RT overnight. The volatile fractions are removed under reduced pressure, and the residue is purified by column chromatography (silica gel, MeOH:DCM=99:1).

Yield: 415 mg; LC/MS (method D): m/z=213 (M+1); Rt=1.121 min

Example 4

4-{(E)-2-[5-(3-Fluorophenyl)pyridin-2-yl]vinyl}-2-methyloctahydropyrrolo[3,4-a]-indolizine-1,3-dione (2 racemic mixtures)

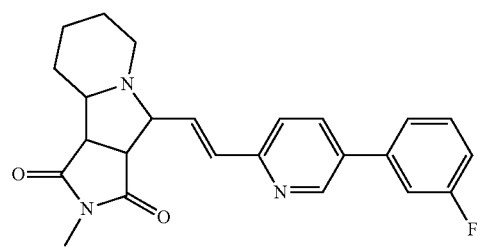 [SMILES: CN1C(=O)C2C(C1=O)C1CCCCN1C2/C=C/c1ccc(-c2cccc(F)c2)cn1]

A mixture of 235 mg of (E)-3-[5-(3-fluorophenyl)pyridin-2-yl]propenal, 133 mg of D-pipecolinic acid, 115 mg of N-methylmaleimide and 30 ml of MeCN is heated at the boil for 2 h. The volatile components are removed under reduced pressure and the residue is purified by column chromatography (silica gel, MeOH:DCM=97:3). In this manner, 2 pure fractions are isolated.

Yields: racemic mixture 1: 275 mg; LC/MS (method D): m/z=406 (M+1); Rt=0.985 min racemic mixture 2: 115 mg; LC/MS (method D): m/z=406 (M+1); Rt=0.994 min Example 5

4-{(E)-2-[5-(3-Fluorophenyl)pyridin-2-yl]vinyl}-2-methyloctahydropyrrolo[3,4-a]-indolizine-1,3-dione (2 diastereomers)

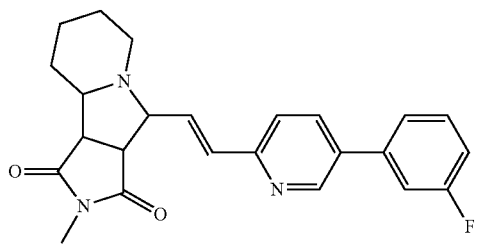 [SMILES: CN1C(=O)C2C(C1=O)C1CCCCN1C2/C=C/c1ccc(-c2cccc(F)c2)cn1]

The racemic mixture 2 from Example 4 is separated by chiral chromatography (HPLC column: Chiralcel OJ-H/62, 250×4.6 mm, mobile phase: MeOH+0.1% diethylamine, flow rate: 1 ml/min, 30° C.), giving 2 pure diastereomers of an absolute configuration which is still unknown.

Yields: diastereomer 1: 43 mg; LCMS: (M+1): 406; Rt=6.27 min diastereomer 2: 42.5 mg; LC/MS: (M+1): 406; Rt=7.64 min Example 6

4-[(E)-2-(5-Bromopyridin-2-yl)vinyl]-2-methyloctahydropyrrolo[3,4-a]indolizine-1,3-dione (3 racemic mixtures)

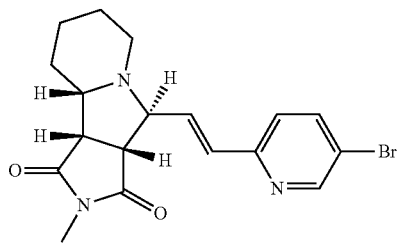

racemic mixture 1

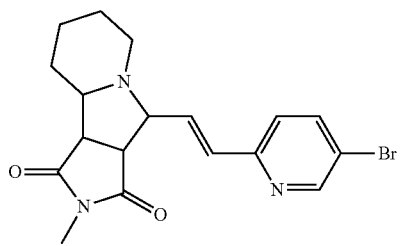

racemic mixture 2

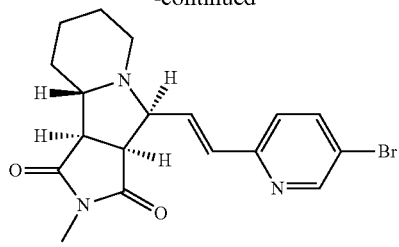

racemic mixture 3

A mixture of 820 mg of (E)-3-(5-bromopyridin-2-yl)propenal, 500 mg of D-pipecolinic acid, 430 mg of N-methylmaleinimide and 20 ml of MeCN is boiled at reflux for 2 h. The solvents are removed and the residue is purified by column chromatography (silica gel, ethyl acetate:DCM=3:1). Using this method, 3 pure fractions are obtained.

Yield: racemic mixture 1: 414 mg; LC/MS (method J): m/z=391 (M+1); Rt=0.598 min racemic mixture 2: 162 mg; LC/MS (method J): m/z=391 (M+1); Rt=0.583 min racemic mixture 3: 385 mg; LC/MS (method J): m/z=391 (M+1); Rt=0.600 min Example 7

7-Hydroxy-2-methyl-4-[(E)-2-(6-methylpyridin-2-yl)vinyl]hexahydropyrrolo[3,4-a]pyrrolizine-1,3-dione (2 racemic mixtures)

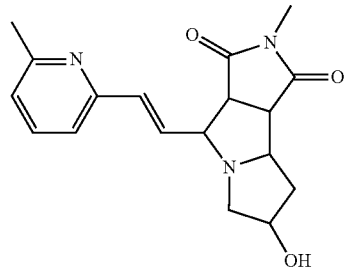 [SMILES: Cc1cccc(/C=C/C2C3C(=O)N(C)C(=O)C3C3CC(O)CN23)n1]

The title compound is prepared analogously from 100 mg of (E)-3-(6-methylpyridin-2-yl)propenal, 75 mg of N-methylmaleimide and 100 mg of cis-4-hydroxy-L-proline.

Yields: racemic mixture 1: 15 mg; LC/MS (method J): m/z=328 (M+1); Rt=0.106 min racemic mixture 2: 173 mg; LC/MS (method J): m/z=328 (M+1); Rt=0.102 min Example 8

2-Methyl-4-[(E)-2-(6-methylpyridin-2-yl)-vinyl]octahydropyrrolo[3,4-a]-indolizine-1,3-dione (3 racemic mixtures)

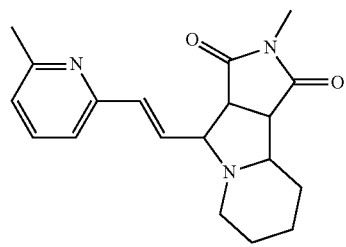 [SMILES: Cc1cccc(/C=C/C2C3C(=O)N(C)C(=O)C3C3CCCCN23)n1]

The title compound is obtained analogously from 100 mg of (E)-3-(6-methylpyridin-2-yl)propenal, 76 mg of N-methylmaleimide and 78 mg of pipecolinic acid. The residue is purified by column chromatography (silica gel, MeOH:DCM=2:98).

Yields: racemic mixture 1: 27 mg; LC/MS (method J): m/z=326 (M+1); Rt=0.164 min racemic mixture 2: 71 mg; LC/MS (method J): m/z=326 (M+1); Rt=0.155 min racemic mixture 3: 44 mg; LC/MS (method J): m/z=326 (M+1); Rt=0.125 min Example 9

2-Methyl-4-[(E)-2-(6-methylpyridin-2-yl)vinyl]hexahydropyrrolo[3,4-a]pyrrolizine-1,3-dione (3 racemic mixtures)

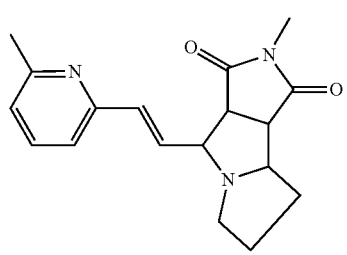 [SMILES: Cc1cccc(/C=C/C2C3C(=O)N(C)C(=O)C3C3CCCN23)n1]

The title compound is obtained analogously from 100 mg of (E)-3-(6-methylpyridin-2-yl)propenal, 76 mg of N-methylmaleimide and 78 mg of L-proline. The residue was purified by column chromatography (silica gel, MeOH:DCM=2:98).

Yields: racemic mixture 1: 38 mg, LC/MS (method J): m/z=312 (M+1); Rt=0.106 min racemic mixture 2: 34 mg; LC/MS (method J): m/z=312 (M+1); Rt=0.114 min racemic mixture 3: 66 mg; LC/MS (method J): m/z=312 (M+1); Rt=0.113 min Example 10 tert-Butyl (8-{(E)-2-[5-(3-fluorophenyl)pyridin-2-yl]vinyl}-2-methyl-1,3-dioxodecahydro-2,5,7a-triazacyclopenta[a]indene-5-carboxylate (2 racemic mixtures)

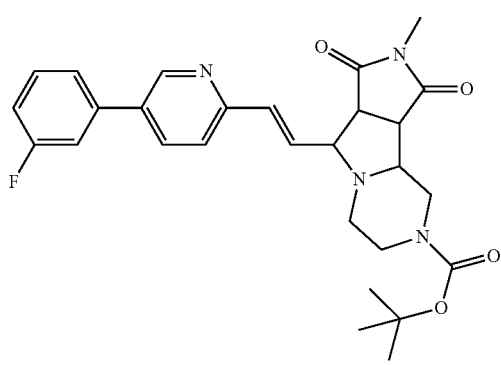 [SMILES: CN1C(=O)C2C(C1=O)C1CN(C(=O)OC(C)(C)C)CCN1C2/C=C/c1ccc(-c2cccc(F)c2)cn1]

A mixture of 50 mg of (E)-3-[5-(3-fluorophenyl)pyridin-2-yl]propenal, 50 mg of 4-Boc-piperazine-2-carboxylic acid, 24 mg of N-methylmaleimide and 2 ml of MeCN is heated at reflux for 2 h. The volatile components are removed under reduced pressure and the residue is purified by column chromatography (silica gel, MeOH:DCM=98:2). In this manner, 2 pure fractions are isolated.

Yields: racemic mixture 1: 11 mg; LC/MS (method J): m/z=507 (M+1); Rt=0.933 min racemic mixture 2: 10 mg; LC/MS (method J): m/z=507 (M+1); Rt=0.879 min Example 11

(S)-4-{(E)-2-[5-(3-Fluorophenyl)pyridin-2-yl]vinyl}-7-hydroxy-2-methylhexahydropyrrolo[3,4-a]pyrrolizine-1,3-dione (4 racemic mixtures)

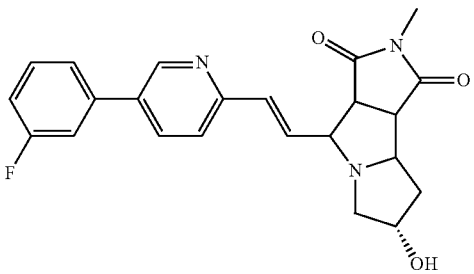 [SMILES: CN1C(=O)C2C(C1=O)C1C[C@H](O)CN1C2/C=C/c1ccc(-c2cccc(F)c2)cn1]

A mixture of 100 mg of (E)-3-[5-(3-fluorophenyl)pyridin-2-yl]propenal, 64 mg of (2S,4S)-4-hydroxypyrrolidine-2-carboxylic acid, 54 mg of N-methylmaleimide and 4 ml of MeCN is heated at the boil for 4 h. The volatile components are removed under reduced pressure and the residue is purified by column chromatography (silica gel, MeOH:DCM=5:95). In this manner, 4 pure fractions are isolated as racemic mixtures.

Yields: racemic mixture 1: 47 mg; LC/MS (method J): m/z=408 (M+1); Rt=0.667 min racemic mixture 2: 17 mg; LC/MS (method J): m/z=408 (M+1); Rt=0.664 min racemic mixture 3: 18 mg; LC/MS (method J): m/z=408 (M+1); Rt=0.667 min racemic mixture 4: 18 mg; LC/MS (method J): m/z=408 (M+1); Rt=0.673 min Example 12

(R)-4-{(E)-2-[5-(3-Fluorophenyl)pyridin-2-yl]vinyl}-7-hydroxy-2-methylhexahydropyrrolo[3,4-a]pyrrolizine-1,3-dione (4 racemic mixtures)

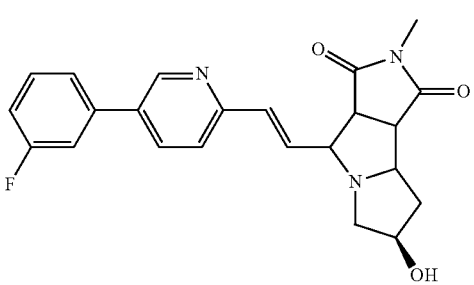 [SMILES: CN1C(=O)C2C(C1=O)C1C[C@@H](O)CN1C2/C=C/c1ccc(-c2cccc(F)c2)cn1]

The title compound is obtained analogously from 100 mg of (E)-3-[5-(3-fluorophenyl)pyridin-2-yl]propenal, 54 mg of N-methylmaleimide and 64 mg of (2S,4R)-4-hydroxypyrrolidine-2-carboxylic acid. The residue is purified by column chromatography (silica gel, MeOH:DCM=5:95). In this manner, 4 pure fractions are isolated as racemic mixtures.

Yields: racemic mixture 1: 12 mg; LC/MS (method J): m/z=408 (M+1); Rt=0.668 min racemic mixture 2: 62 mg; LC/MS (method J): m/z=408 (M+1); Rt=0.665 min racemic mixture 3: 18 mg; LC/MS (method J): m/z=408 (M+1); Rt=0.669 min racemic mixture 4: 32 mg; LC/MS (method J): m/z=408 (M+1); Rt=0.672 min Example 13

6-{(E)-2-[5-(3-Fluorophenyl)pyridin-2-yl]vinyl}-8-methylhexahydropyrrolo[3',4':3,4]pyrrolo[2,1-c][1,4]oxazine-7,9-dione (3 racemic mixtures)

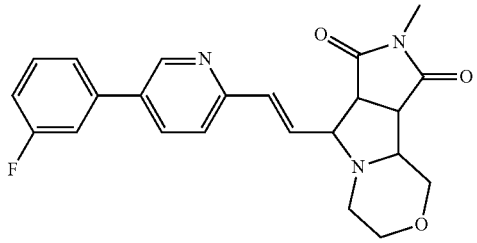

The title compound is obtained analogously from 100 mg of (E)-3-[5-(3-fluorophenyl)pyridin-2-yl]propenal, 49 mg of N-methylmaleimide and 58 mg of morpholine-3-carboxylic acid. The crude product is purified by column chromatography (silica gel, MeOH:DCM=2:98). In this manner, 3 pure fractions are isolated as racemic mixtures.

Yields: racemic mixture 1: 40 mg; LC/MS (method J): m/z=408 (M+1); Rt=0.738 min racemic mixture 2: 39 mg; LC/MS (method J): m/z=408 (M+1); Rt=0.735 min racemic mixture 3: 20 mg; LC/MS (method J): m/z=408 (M+1); Rt=0.697 min Example 14

2-Ethyl-4-{(E)-2-[5-(3-fluorophenyl)pyridin-2-yl]vinyl}octahydropyrrolo[3,4-a]indolizine-1,3-dione (3 racemic mixtures)

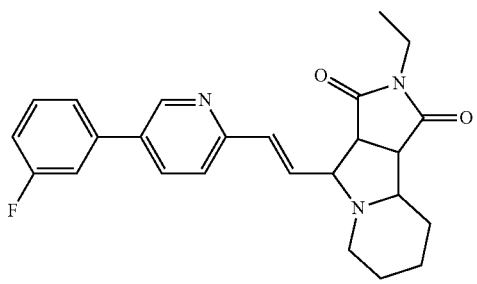 [SMILES: CCN1C(=O)C2C(C1=O)C1CCCCN1C2/C=C/c1ccc(-c2cccc(F)c2)cn1]

The title compound is obtained analogously from 100 mg of (E)-3-[5-(3-fluorophenyl)pyridin-2-yl]propenal, 55 mg of N-ethylmaleimide and 57 mg of D,L-pipecolinic acid. The crude product is purified by column chromatography (silica gel, MeOH:DCM=1:99). In this manner, 3 pure fractions are isolated as racemic mixtures.

Yields: racemic mixture 1: 58 mg; LC/MS (method J): m/z=420 (M+1); Rt=0.747 min racemic mixture 2: 16 mg; LC/MS (method J): m/z=420 (M+1); Rt=0.758 min racemic mixture 3: 56 mg; LC/MS (method J): m/z=420 (M+1); Rt=0.745 min Example 15

4-{(E)-2-[5-(3-Fluorophenyl)pyridin-2-yl]vinyl}-2-methylhexahydropyrrolo[3,4-a]-pyrrolizine-1,3-dione (3 racemic mixtures)

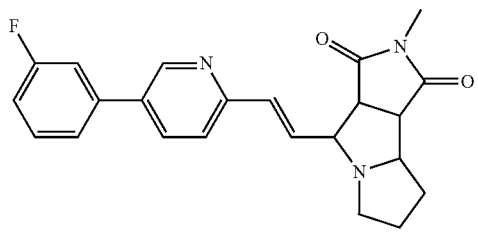 [SMILES: CN1C(=O)C2C(C1=O)C1CCCN1C2/C=C/c1ccc(-c2cccc(F)c2)cn1]

The title compound is obtained analogously from 100 mg of (E)-3-[5-(3-fluorophenyl)pyridin-2-yl]propenal, 49 mg of N-methylmaleimide and 51 mg of D,L-proline. The crude product is purified by column chromatography (silica gel, MeOH:DCM=1:99). In this manner, 3 pure fractions are isolated as racemic mixtures.

Yields: racemic mixture 1: 8 mg; LC/MS (method J): m/z=392 (M+1); Rt=0.955 min racemic mixture 2: 57 mg; LC/MS (method J): m/z=392 (M+1); Rt=0.959 min racemic mixture 3: 100 mg; LC/MS (method J): m/z=392 (M+1); Rt=0.954 min Example 16

5-{(E)-2-[5-(3-Fluorophenyl)pyridin-2-yl]vinyl}-7-methyltetrahydropyrrolo[3',4':3,4]-pyrrolo[1,2-c]thiazole-6,8-dione (3 racemic mixtures)

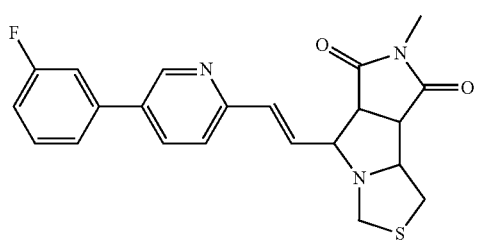 [SMILES: CN1C(=O)C2C(C1=O)C1CSCN1C2/C=C/c1ccc(-c2cccc(F)c2)cn1]

The title compound is obtained analogously from 100 mg of (E)-3-[5-(3-fluorophenyl)pyridin-2-yl]propenal, 49 mg of N-methylmaleimide and 59 mg of D-thiazolidine-4-carboxylic acid. The crude product is purified by column chromatography (silica gel, MeOH:DCM=3:97). In this manner, 3 pure fractions are isolated as racemic mixtures.

Yields: racemic mixture 1: 25 mg; LC/MS (method J): m/z=410 (M+1); Rt=0.814 min racemic mixture 2: 37 mg; LC/MS (method J): m/z=410 (M+1); Rt=0.824 min racemic mixture 3: 24 mg; LC/MS (method J): m/z=410 (M+1); Rt=0.809 min Example 17

2-Methyl-4-{(E)-2-[5-(3-trifluoromethyl phenyl)pyridin-2-yl]vinyl}octahydropyrrolo[3,4-a]indolizine-1,3-dione (racemic mixture)

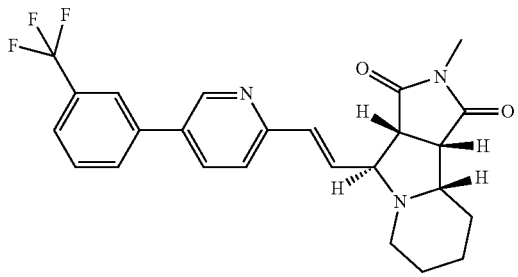 [SMILES: CN1C(=O)[C@@H]2[C@H](C1=O)[C@@H]1CCCCN1[C@H]2/C=C/c1ccc(-c2cccc(C(F)(F)F)c2)cn1]

A mixture consisting of 42 mg of 4-[(E)-2-(5-bromopyridin-2-yl)vinyl]-2-methyloctahydropyrrolo[3,4-a]indolizine-1,3-dione (from Example 6, racemic mixture 1), 2.5 mg of tetrakis(triphenylphosphine)palladium(0), 25 mg of 3-trifluoromethylphenylboronic acid, 37 mg of potassium carbonate, 1.5 ml of toluene, 0.3 ml of ethanol and 0.75 ml of water is stirred at 100° C. for 5 h. After cooling, the mixture is taken up in 20 ml of water and the product is extracted by shaking with 20 ml of ethyl acetate. After drying and concentration of the organic phase, an oil is obtained. The crude product is purified by column chromatography (silica gel, MeOH:DCM=1:99).

Yield: 36 mg; LC/MS (method J): m/z=456 (M+1); Rt=0.80 min

Example 18

2-Methyl-4-{(E)-2-[5-(3-trifluoromethylphenyl)pyridin-2-yl]vinyl}octahydropyrrolo[3,4-a]indolizine-1,3-dione (racemic mixture)

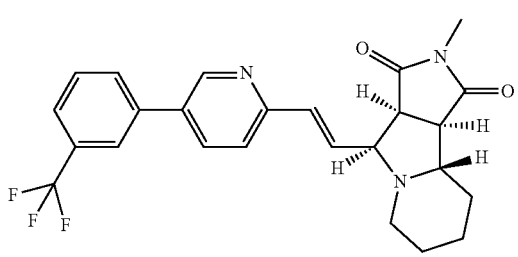 [SMILES: CN1C(=O)[C@@H]2[C@H](C1=O)[C@H](/C=C/c1ccc(-c3cccc(C(F)(F)F)c3)cn1)N1CCCC[C@@H]21]

The title compound is prepared analogously to the compound from Example 17 from 45 mg of 4-[(E)-2-(5-bromopyridin-2-yl)vinyl]-2-methyloctahydropyrrolo[3,4-a]indolizine-1,3-dione (from Example 6, racemic mixture 3) and 26 mg of 3-trifluoromethylphenylboronic acid.

Yield: 33 mg; LC/MS (method J): m/z=456 (M+1); Rt=0.799 min

Example 19

4-{(E)-2-[5-(2-Methoxyphenyl)pyridin-2-yl]vinyl}-2-methyloctahydropyrrolo[3,4-a]-indolizine-1,3-dione (racemic mixture)

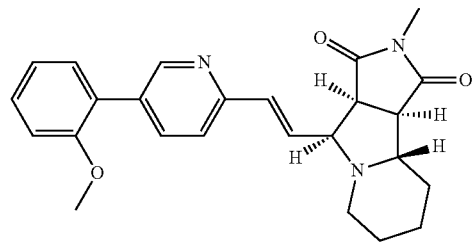 [SMILES: COc1ccccc1-c1ccc(/C=C/[C@H]2[C@H]3C(=O)N(C)C(=O)[C@H]3[C@@H]3CCCCN23)nc1]

The title compound is prepared analogously to the compound from Example 17 from 42 mg of 4-[(E)-2-(5-bromopyridin-2-yl)vinyl]-2-methyloctahydropyrrolo[3,4-a]-indolizine-1,3-dione (from Example 6, racemic mixture 3) and 18 mg of 2-methoxyphenylboronic acid.

Yield: 15 mg; LC/MS (method J): m/z=418 (M+1); Rt=0.674 min

Example 20

4-{(E)-2-[5-(2-Chlorophenyl)pyridin-2-yl]vinyl}-2-methyloctahydropyrrolo[3,4-a]-indolizine-1,3-dione (racemic mixture)

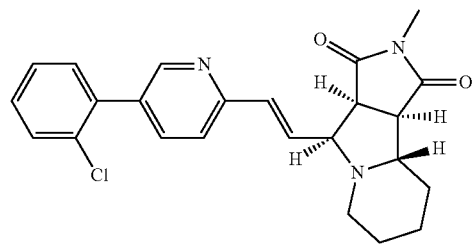 [SMILES: CN1C(=O)[C@@H]2[C@H](C1=O)[C@H](/C=C/c1ccc(-c3ccccc3Cl)cn1)N1CCCC[C@@H]21]

The title compound is prepared analogously to the compound from Example 17 from 42 mg of 4-[(E)-2-(5-bromopyridin-2-yl)vinyl]-2-methyloctahydropyrrolo[3,4-a]-indolizine-1,3-dione (from Example 6, racemic mixture 3) and 18 mg of 2-chloro-phenylboronic acid.

Yield: 7 mg; LC/MS (method D): m/z=422 (M+1); Rt=1.044 min

Example 21

2-Methyl-4-[(E)-2-(5-thiophen-3-ylpyridin-2-yl)vinyl]octahydropyrrolo[3,4-a]indolizine-1,3-dione (racemic mixture)

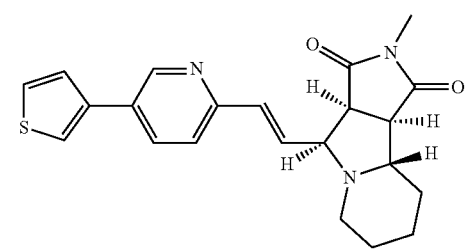 [SMILES: CN1C(=O)[C@@H]2[C@H](C1=O)[C@H](/C=C/c1ccc(-c3ccsc3)cn1)N1CCCC[C@@H]21]

The title compound is prepared analogously to the compound from Example 17 from 42 mg of 4-[(E)-2-(5-bromopyridin-2-yl)vinyl]-2-methyloctahydropyrrolo[3,4-a]-indolizine-1,3-dione (from Example 6, racemic mixture 3) and 15 mg of 3-thiophene-boronic acid.

Yield: 15 mg; LC/MS (method J): m/z=394 (M+1); Rt=0.617 min

Example 22

4-{(E)-2-[5-(3-Fluorophenyl)pyridin-2-yl]vinyl}-2-methyl-3a,4,6,9,9a,9b-hexahydropyrrolo[3,4-a]indolizine-1,3-dione (3 racemic mixtures)

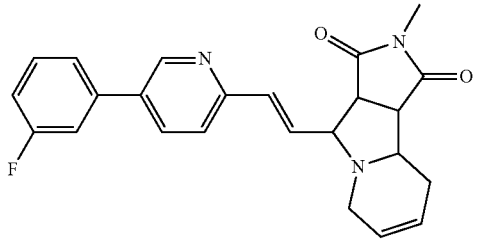 [SMILES: CN1C(=O)C2C(C1=O)C1CC=CCN1C2/C=C/c1ccc(-c2cccc(F)c2)cn1]

The title compound is prepared analogously from 100 mg of (E)-3-[5-(3-fluorophenyl)pyridin-2-yl]propenal, 49 mg of N-methylmaleimide and 58 mg of 1,2,3,6-tetrahydropyridine-2-carboxylic acid hydrochloride. The crude product is purified by column chromatography (silica gel, MeOH:DCM=2:98). In this manner, 3 pure fractions are isolated as racemic mixtures.

Yields: racemic mixture 1: 11 mg; LC/MS (method J): m/z=404 (M+1); Rt=0.687 min racemic mixture 2: 10 mg; LC/MS (method J): m/z=404 (M+1); Rt=0.691 min racemic mixture 3: 20 mg; LC/MS (method J): m/z=404 (M+1); Rt=0.6692 min Example 23

2-Cyclopropyl-4-{(E)-2-[5-(3-fluorophenyl)pyridin-2-yl]vinyl}octahydropyrrolo[3,4-a]-indolizine-1,3-dione (2 racemic mixtures)

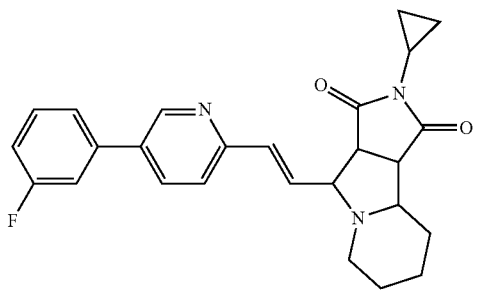 [SMILES: O=C1C2C(C(=O)N1C1CC1)C1CCCCN1C2/C=C/c1ccc(-c2cccc(F)c2)cn1]

The title compound is obtained in an analogous manner from 80 mg of (E)-3-[5-(3-fluorophenyl)pyridin-2-yl]propenal, 30 mg of N-cyclopropylmaleimide and 45 mg of D,L-pipecolinic acid. The crude product is purified by column chromatography (silica gel, MeOH:DCM=2:98). In this manner, 2 pure fractions are isolated as racemic mixtures.

Yields: racemic mixture 1: 50 mg; LC/MS (method J): m/z=432 (M+1); Rt=0.732 min racemic mixture 2: 10 mg; LC/MS (method J): m/z=432 (M+1); Rt=0.736 min Example 24

8-{(E)-2-[5-(3-Fluorophenyl)pyridin-2-yl]vinyl}-2-methyloctahydro-2,5,7a-triazacyclopenta[a]indene-1,3-dione trifluoroacetic acid salt

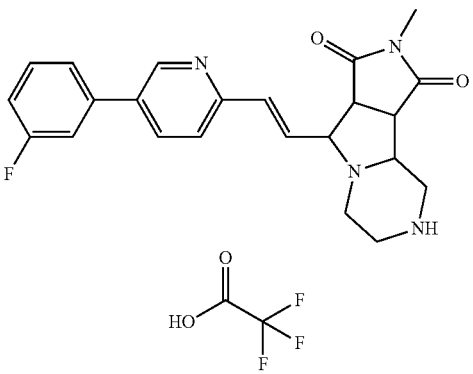

100 mg of tert-butyl (8-{(E)-2-[5-(3-fluorophenyl)pyridin-2-yl]vinyl}-2-methyl-1,3-dioxodecahydro-2,5,7a-triazacyclopenta[a]indene-5-carboxylate (from Example 10) are dissolved in 9 ml of dichloromethane, and 3 ml of trifluoroacetic acid are added. The mixture is stirred at RT for 2 h, the solvent is then removed under reduced pressure and the crude product is purified by column chromatography (silica gel, MeOH:DCM).

Yield: 120 mg; LC/MS (method J): m/z=407 (M+1); Rt=0.595 min

Pharmacological Examples

PAR1 Determination Method: Inhibition of PAR1-Mediated Platelet Aggregation

The pharmacological testing of the substances took place in platelet aggregation induced by TRAP (thrombin receptor-activating peptide) in 96-well format. For this purpose, blood was taken from healthy volunteers in 20 ml syringes containing 2 ml of 3.13% strength sodium citrate solution. After centrifugation at 150×g for 20 minutes, the platelet-rich plasma (PRP) was separated off and mixed with 1 μl of PGE1 solution (500 μg/ml in ethanol)/ml of PRP. Incubation at RT for 5 minutes was followed by centrifugation at 120×g for 15 minutes to remove the leukocytes. The leukocyte-free PRP was transferred in 5 ml portions into 15 ml PP tubes and centrifuged at 360×g for 15 minutes in order to pellet the platelets. The plasma was then decanted off and the platelet sediment from 5 ml of PRP was resuspended in 1 ml of Tyrode's (120 mM NaCl, 2.6 mM KCl, 12 mM NaHCO$_3$, 0.39 mM NaH$_2$PO$_4$×H$_2$O, 10 mM HEPES, 0.35% BSA (Bovine Serum Albumin), 5.5 mM glucose, pH 7.4) and adjusted with Tyrode's to a platelet count of 3×10$^5$/microliter (μl). 13 ml of this cell suspension were then mixed with 866 μl of 10 mM CaCl$_2$ solution, and 120 μl thereof were pipetted into each well of a 96-well plate containing 15 μl of the substance to be tested. After incubation at RT in the dark for 30 minutes, 15 μl of a TRAP solution (70-100 μM) were added as agonist, and kinetics were recorded at 650 nm in a SpectraMax 340 at 37° C. for 20 minutes while shaking. The areas under the curves of negative control (Tyrode's/DMSO) and positive control (15 µl of agonist DMSO) were calculated and the difference was fixed as the 100% value. The substances to be tested were pipetted as serial dilutions in duplicate determination, the AUC was likewise determined for each substance concentration, and the % inhibition of the AUC compared with the control was calculated. On the basis of the % inhibition, the $IC_{50}$ was calculated by nonlinear regression analysis according to the 4-parameter equation. Table 1 shows results ($IC_{50}$ values in micromol/l).

TABLE 1

| Compound from Example | Inhibition of platelet aggregation $IC_{50}$ [micro M] |
|---|---|
| 11 (Fr. 2) | 15.8 |
| 13 (Fr. 3) | 7.1 |
| 14 (Fr. 3) | 3.68 |
| 18 | 3.23 |
| 19 | 4.09 |
| 20 | 0.26 |

"Fr." denotes the number of the racemic mixture (fraction) described in the example

What is claimed is:
1. A compound of formula I

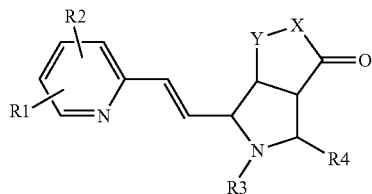

or a physiologically acceptable salt of the compound of formula I, where
R1 and R2 are identical or different and are independently of one another hydrogen, —($C_1$-$C_6$)-alkyl, —O—($C_1$-$C_6$)-alkyl, aryl, halogen or hetaryl, where alkyl, aryl and hetaryl are in each case unsubstituted or mono-, di- or trisubstituted independently of one another by F, Cl, Br, CN, —($C_1$-$C_4$)-alkyl, —NH—($C_1$-$C_4$)-alkyl, —N(($C_1$-$C_4$)-alkyl)$_2$, —NH$_2$, —OH, —O—CF$_3$, —S—CF$_3$ or —CF$_3$, or
R3 and R4 together with the ring atoms to which they are respectively attached form a saturated or unsaturated 5-membered to 7-membered ring, where the ring consists only of carbon atoms except for the nitrogen atom which carries the group R3, or 1 or 2 of these carbon atoms are replaced by O, S, SO, SO$_2$ or N—R5, where the ring is unsubstituted or mono-, di- or trisubstituted independently of one another by F, Cl, —OH, —NH—R7, —($C_1$-$C_4$)-alkyl, —O—($C_1$-$C_4$)-alkyl, C(O)—O—($C_1$-$C_4$)-alkyl, aryl or hetaryl;
X is N—R6;
Y is C(O), CH$_2$, CH—CH$_3$ or C(CH$_3$)$_2$;
R5 is hydrogen, —C(O)—($C_1$-$C_4$)-alkyl, —C(O)—O—($C_1$-$C_4$)-alkyl, —($C_1$-$C_6$)-alkyl, —($C_2$-$C_4$)-alkyl-O—($C_1$-$C_4$)-alkyl, —($C_2$-$C_4$)-alkyl-OH, aryl or hetaryl;
R7 is hydrogen, —C(O)—($C_1$-$C_4$)-alkyl, —C(O)—O—($C_1$-$C_4$)-alkyl, —($C_1$-$C_6$)-alkyl, —($C_2$-$C_4$)-alkyl-O—($C_1$-$C_4$)-alkyl, —($C_2$-$C_4$)-alkyl-OH, aryl or hetaryl; and R6 is hydrogen, —($C_1$-$C_6$)-alkyl, —($C_3$-$C_7$)-cycloalkyl, —($C_1$-$C_4$)-alkylene-aryl or C(O)—O—($C_1$-$C_4$)-alkyl.
2. The compound of formula I as claimed in claim 1, or a physiologically acceptable salt of the compound of formula I, where
R1 and R2 are identical or different and are independently of one another hydrogen, —($C_1$-$C_6$)-alkyl, —O—($C_1$-$C_6$)-alkyl, aryl, halogen or hetaryl, where alkyl, aryl and hetaryl are in each case unsubstituted or mono-, di- or trisubstituted independently of one another by F, Cl, Br, CN, —($C_1$-$C_4$)-alkyl, —O—($C_1$-$C_4$)-alkyl, —NH—($C_1$-$C_4$)-alkyl, —N(($C_1$-$C_4$)-alkyl)$_2$ or —CF$_3$, or
R3 and R4 together with the ring atoms to which they are respectively attached form a saturated or unsaturated 5-membered to 7-membered ring selected from the group consisting of azepine, [1,2]diazepine, [1,3]diazepine, [1,4]diazepine, dihydroimidazolone, imidazole, imidazoline, imidazolidine, imidazolidinone, isothiazole, isothiazolidine, isothiazoline, isoxazole, isoxazoline, isoxazolidine, morpholine, oxathiazine dioxide, [1,2]oxazine, [1,3]oxazine, [1,4]oxazine, oxazolone, oxazole, oxazolidine, piperazine, piperidine, pyrazine, pyrazole, pyrazoline, pyrazolidine, pyridazine, pyridine, pyridinone, pyridopyrazines, pyridopyridines, pyrimidine, pyrrole, pyrrolidine, pyrrolidinone, pyrroline, 1,2,3,6-tetrahydropyridine, [1,2]thiazine, [1,3]thiazine, [1,4]thiazine, [1,3]thiazole, thiazole or thiazolidine, where the ring is unsubstituted or mono-, di- or trisubstituted independently of one another by F, Cl, —OH, —($C_1$-$C_4$)-alkyl, —O—($C_1$-$C_4$)-alkyl, C(O)—O—($C_1$-$C_4$)-alkyl, aryl or hetaryl;
X is N—R6;
Y is C(O), CH$_2$ or CH—CH$_3$; and
R6 is hydrogen, —($C_1$-$C_6$)-alkyl, —($C_3$-$C_7$)-cycloalkyl or —($C_1$-$C_4$)-alkylene-aryl.
3. The compound of formula I as claimed in claim 1, or a physiologically acceptable salt of the compound of formula I, where
R1 and R2 are identical or different and are independently of one another hydrogen, —($C_1$-$C_4$)-alkyl, —O—($C_1$-$C_4$)-alkyl, Br, F, Cl, aryl or hetaryl, where hetaryl is selected from the group consisting of acridinyl, azepinyl, azetidinyl, aziridinyl, benzimidazolyl, benzofuranyl, benzothiofuranyl, benzothiophenyl, benzoxazolyl, benzthiazolyl, benztriazolyl, benzisoxazolyl, benzisothiazolyl, carbazolyl, 4aH-carbazolyl, carbolinyl, quinazolinyl, quinolinyl, 4H-quinolizinyl, quinoxalinyl, quinuclidinyl, chromanyl, chromenyl, cinnolinyl, decahydroquinolinyl, dibenzofuranyl, dibenzothiophenyl, dihydrofuran[2,3-b]-tetrahydrofuranyl, dihydrofuranyl, dioxolyl, dioxanyl, 2H,6H-1,5,2-dithiazinyl, furanyl, furazanyl, imidazolidinyl, imidazolinyl, imidazolyl, 1H-indazolyl, indolinyl, indolizinyl, indolyl, 3H-indolyl, isobenzofuranyl, isoquinolinyl, isochromanyl, isoindazolyl, isoindolinyl, isoindolyl, isothiazolidinyl, 2-isothiazolinyl, isothiazolyl, isoxazolyl, isoxazolidinyl, 2-isoxazolinyl, morpholinyl, naphthyridinyl, octahydroisoquinolinyl, 1,2,3-oxadiazolyl, 1,2,4-oxadiazolyl, 1,2,5-oxadiazolyl, 1,3,4-oxadiazolyl, oxazolidinyl, oxazolyl, oxothiolanyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyroazolidinyl, pyrazolinyl, pyrazolyl, pyridazinyl, pryidooxazolyl, pyridoimidazolyl, pyridothiazolyl, pyridothiophenyl, pyridyl, pyrimidinyl, pyrrolidinyl, pyrrolinyl, 2H-pyrrolyl, pyrrolyl, tetrahydrofuranyl, tetrahydroisoquinolinyl, tetrahydroquinolinyl, tetrahydropyridinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolidinyl, thiazolinyl, thiazolyl, thienyl, thienoimidazolyl, thienooxazolyl, thienopyrrolyl, thienopyridinyl, thienothiazolyl, thienothiophenyl, thiomorpholinyl, triazinyl, 1,2,3-triazolyl, 1,2,4-triazolyl, 1,2,5-triazolyl, 1,3,4-triazolyl and xanthenyl, where alkyl, aryl and hetaryl are in each case unsubstituted or mono-, di- or trisubstituted independently of one another by F, Cl, CN, —($C_1$-$C_4$)-alkyl, —O—($C_1$-$C_4$)-alkyl, —N(($C_1$-$C_4$)-alkyl)$_2$ or —$CF_3$;

R3 and R4 together with the ring atoms to which they are respectively attached form a saturated or unsaturated 5-membered to 7-membered ring selected from the group consisting of azepine, [1,2]diazepine, [1,3]diazepine, [1,4]diazepine, dihydroimidazolone, imidazole, imidazoline, imidazolidine, imidazolidinone, isothiazole, isothiazolidine, isothiazoline, isoxazole, isoxazoline, isoxazolidine, morpholine, oxathiazine dioxide, [1,2]oxazine, [1,3]oxazine, [1,4]oxazine, oxazolone, oxazole, oxazolidine, piperazine, piperidine, pyrazine, pyrazole, pyrazoline, pyrazolidine, pyridazine, pyridine, pyridinone, pyrimidine, pyrrole, pyrrolidine, pyrrolidinone, pyrroline, 1,2,3,6-tetrahydropyridine, [1,2]thiazine, [1,3]thiazine, [1,4]thiazine, [1,3]thiazole, thiazole and thiazolidine, where the ring is unsubstituted or mono-, di- or trisubstituted independently of one another by F, Cl, —OH, —($C_1$-$C_4$)-alkyl, C(O)—O—($C_1$-$C_4$)-alkyl, aryl or hetaryl;

X is N—R6;

Y is C(O), $CH_2$ or CH—$CH_3$; and

R6 is hydrogen, —($C_1$-$C_6$)-alkyl, —($C_3$-$C_6$)-cycloalkyl or —($C_1$-$C_4$)-alkylene-aryl.

4. The compound of formula I as claimed in claim 1, or a physiologically acceptable salt of the compound of formula I, where R1 and R2 are identical or different and are independently of one another hydrogen, —($C_1$-$C_4$)-alkyl, Br, thienyl or phenyl, where thienyl and phenyl are in each case unsubstituted or mono- or disubstituted independently of one another by F, Cl, —O-methyl or —$CF_3$;

R3 and R4 together with the ring atoms to which they are respectively attached form a saturated or unsaturated 5-membered to 6-membered ring selected from the group consisting of azepine, [1,2]diazepine, [1,3]diazepine, [1,4]diazepine, dihydroimidazolone, imidazole, imidazoline, imidazolidine, imidazolidinone, isothiazole, isothiazolidine, isothiazoline, isoxazole, isoxazoline, isoxazolidine, morpholine, oxathiazine dioxide, [1,2]oxazine, [1,3]oxazine, [1,4]oxazine, oxazolone, oxazole, oxazolidine, piperazine, piperidine, pyrazine, pyrazole, pyrazoline, pyrazolidine, pyridazine, pyridine, pyridinone, pyrimidine, pyrrole, pyrrolidine, pyrrolidinone, pyrroline, 1,2,3,6-tetrahydropyridine, [1,2]thiazine, [1,3]thiazine, [1,4]thiazine, [1,3]thiazole, thiazole and thiazolidine, where the ring is unsubstituted or mono-, di- or trisubstituted independently of one another by F, —OH, C(O)—O—($C_1$-$C_4$)-alkyl, phenyl or hetaryl;

X is N—R6;

Y is C(O), $CH_2$ or CH—$CH_3$; and

R6 is hydrogen, —($C_1$-$C_6$)-alkyl, —($C_3$-$C_6$)-cycloalkyl or —($C_1$-$C_4$)-alkylene-phenyl.

5. The compound of formula I as claimed in claim 1, or a physiologically acceptable salt of the compound of formula I, where R1 and R2 are identical or different and are independently of one another hydrogen, —($C_1$-$C_4$)-alkyl, Br, thienyl or phenyl, where thienyl and phenyl are in each case unsubstituted or mono- or disubstituted independently of one another by F, Cl, —O-methyl or —$CF_3$;

R3 and R4 together with the ring atoms to which they are respectively attached form a saturated or unsaturated 5-membered to 6-membered ring selected from the group consisting of morpholine, piperazine, piperidine, pyrrolidine, 1,2,3,6-tetrahydropyridine and [1,3]thiazole, where the ring is unsubstituted or mono-, di- or trisubstituted independently of one another by F, —OH, phenyl or C(O)—O—($C_1$-$C_4$)-alkyl;

X is N—R6;

Y is C(O), $CH_2$ or CH—$CH_3$; and

R6 is hydrogen, —($C_1$-$C_6$)-alkyl, cyclopropyl or —($C_1$-$C_4$)-alkylene-phenyl.

6. The compound of formula I as claimed in claim 1, or a physiologically acceptable salt of the compound of formula I, where the compound of formula I is selected from the group consisting of:

4-{(E)-2-[5-(3-fluorophenyl)pyridin-2-yl]vinyl}-2-methyloctahydropyrrolo[3,4-a]indolizine-1,3-dione, 4-[(E)-2-(5-bromopyridin-2-yl)vinyl]-2-methyloctahydropyrrolo[3,4-a]indolizine-1,3-dione, 7-hydroxy-2-methyl-4-[(E)-2-(6-methylpyridin-2-yl)vinyl]hexahydropyrrolo[3,4-a]-pyrrolizine-1,3-dione, 2-methyl-4-[(E)-2-(6-methylpyridin-2-yl)vinyl]octahydropyrrolo[3,4-a]indolizine-1,3-dione, 2-methyl-4-[(E)-2-(6-methylpyridin-2-yl)vinyl]hexahydropyrrolo[3,4-a]pyrrolizine-1,3-dione, tert-butyl (8-{(E)-2-[5-(3-fluorophenyl)pyridin-2-yl]vinyl}-2-methyl-1,3-dioxodecahydro-2,5,7a-triazacyclopenta[a]indene-5-carboxylate, (S)-4-{(E)-2-[5-(3-fluorophenyl)pyridin-2-yl]vinyl}-7-hydroxy-2-methylhexahydropyrrolo[3,4-a]pyrrolizine-1,3-dione, (R)-4-{(E)-2-[5-(3-fluorophenyl)pyridin-2-yl]vinyl}-7-hydroxy-2-methylhexahydropyrrolo[3,4-a]pyrrolizine-1,3-dione, 6-{(E)-2-[5-(3-fluorophenyl)pyridin-2-yl]vinyl}-8-methylhexahydropyrrolo[3',4':3,4]-pyrrolo[2,1-c][1,4]oxazine-7,9-dione, 2-ethyl-4-{(E)-2-[5-(3-fluorophenyl)pyridin-2-yl]vinyl}octahydropyrrolo[3,4-a]indolizine-1,3-dione, 4-{(E)-2-[5-(3-fluorophenyl)pyridin-2-yl]vinyl}-2-methylhexahydropyrrolo[3,4-a]pyrrolizine-1,3-dione, 5-{(E)-2-[5-(3-fluorophenyl)pyridin-2-yl]vinyl}-7-methyltetrahydropyrrolo[3',4':3,4]-pyrrolo[1,2-c]thiazole-6,8-dione, 2-methyl-4-{(E)-2-[5-(3-trifluoromethyl-phenyl)pyridin-2-yl]vinyl}octahydropyrrolo[3,4-a]-indolizine-1,3-dione, 4-{(E)-2-[5-(2-methoxyphenyl)pyridin-2-yl]vinyl}-2-methyloctahydropyrrolo[3,4-a]indolizine-1,3-dione, 4-{(E)-2-[5-(2-chlorophenyl)pyridin-2-yl]vinyl}-2-methyloctahydropyrrolo[3,4-a]indolizine-1,3-dione, 2-methyl-4-[(E)-2-(5-thiophen-3-ylpyridin-2-yl)vinyl]octahydropyrrolo[3,4-a]indolizine-1,3-dione, 4-{(E)-2-[5-(3-fluorophenyl)pyridin-2-yl]vinyl}-2-methyl-3a,4,6,9,9a,9b-hexahydropyrrolo[3,4-a]indolizine-1,3-dione, 2-cyclopropyl-4-{(E)-2-[5-(3-fluorophenyl)pyridin-2-yl]vinyl}octahydropyrrolo[3,4-a]-indolizine-1,3-dione, and 8-{(E)-2-[5-(3-fluorophenyl)pyridin-2-yl]vinyl}-2-methyloctahydro-2,5,7a-triazacyclopenta[a]indene-1,3-dione.

7. A pharmaceutical composition comprising an effective amount of at least one compound of formula I or a physiologically acceptable salt thereof as claimed in claim 1 and a pharmaceutically suitable and physiologically acceptable carrier.

8. A pharmaceutical composition comprising an effective amount of at least one compound of formula I or a physiologically acceptable salt thereof as claimed in claim 6 and a pharmaceutically suitable and physiologically acceptable carrier.

9. A process for preparing a compound of formula I or a physiologically acceptable salt thereof as claimed in claim 1, which comprises a) reacting a compound of formula II,

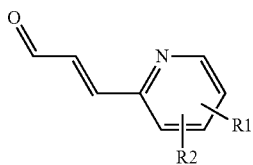

II where the radicals R1 and R2 are as defined in formula I in claim 1, with a compound of formula III and a compound of formula IV,

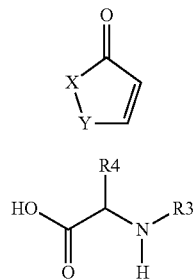

III

IV where the radicals X, Y, R3 and R4 are as defined in formula I in claim 1, in the presence of a solvent at 20° C. to 120° C. to give a compound of formula I; or b) reacting a compound of the formula V,

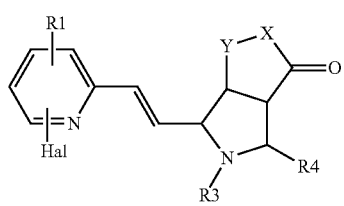

V where the radicals X, Y, R1, R3 and R4 are as defined in formula I in claim 1 and Hal has the meaning of chlorine, bromine, iodine or triflate, with a compound of formula R2-B(OH)$_2$ in the presence of a base and of a suitable metal catalyst in a suitable solvent or solvent mixture to give a compound of formula I; or c) reacting a compound of formula I in which X has the meaning of NH with a suitable alkylating agent in the presence of a base and in a suitable inert solvent at room temperature or at elevated temperature to give the compound of formula I in which X has the meaning of N—R6 and R6 is —($C_1$-$C_6$)-alkyl, —($C_3$-$C_7$)-cycloalkyl or —($C_1$-$C_4$)-alkylene-aryl; or d) fractionating the compound of formula I which has been prepared by processes a) to c), or a suitable precursor of formula I which, owing to its chemical structure, occurs in enantiomeric or diastereomeric forms, by salt formation with enantiomerically pure acids or bases, chromatography on chiral stationary phases or derivatization by means of chiral enantiomerically pure compounds such as amino acids, separation of the diastereomers obtained in this way, and elimination of the chiral auxiliary groups, into the pure enantiomers or diastereomers; or e) either isolating the compound of formula I prepared by processes a) to d) in free form or liberating it from non-physiologically acceptable salts or, in the case where acidic or basic groups are present, converting it into a physiologically acceptable salt.

* * * * *